US008455553B2

(12) United States Patent
David

(10) Patent No.: US 8,455,553 B2
(45) Date of Patent: Jun. 4, 2013

(54) METHODS AND COMPOSITIONS FOR PREVENTION AND TREATMENT OF INFLAMMATORY DISEASE, AUTOIMMUNE DISEASE AND TRANSPLANT REJECTION

(75) Inventor: Michael David, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/293,876

(22) Filed: Nov. 10, 2011

(65) Prior Publication Data

US 2012/0071561 A1    Mar. 22, 2012

Related U.S. Application Data

(63) Continuation of application No. 12/843,410, filed on Jul. 26, 2010, now Pat. No. 8,080,527, which is a continuation of application No. 10/494,452, filed as application No. PCT/US02/35153 on Nov. 2, 2002, now Pat. No. 7,811,996.

(60) Provisional application No. 60/336,759, filed on Nov. 2, 2001.

(51) Int. Cl.
*A61K 31/09* (2006.01)
*A61P 29/00* (2006.01)

(52) U.S. Cl.
USPC ........................................ 514/720; 514/733

(58) Field of Classification Search
USPC .................................. 514/720, 733
See application file for complete search history.

(56) References Cited

U.S. PATENT DOCUMENTS 5,500,367 A    3/1996    Hain et al.

FOREIGN PATENT DOCUMENTS

| WO | WO 99/01148 | 1/1999 |
| WO | WO 99/56737 | * 11/1999 |
| WO | WO 99/59561 | 11/1999 |
| WO | WO 9956737 | * 11/1999 |
| WO | WO 0205825 | 1/2002 |
| WO | WO 02/32410 | 4/2002 |

OTHER PUBLICATIONS

The Merck Manual 16th Ed. 1992, pp. 646-647, pp. 830-831 and p. 1488.*
The Merck Manual, 16th Edn., 1992, pp. 1488-1490.*
Gaut, J.P. et al., PNAS, 2001, 98(21), 11961-11966.
Holzheimer, J. Chemotherapy, 2001, 13(1), 159-172.
Tsai et al., roc. Natl, Sci. Counc., 1999, 23(3), 99-106.
Lin et al., British Pharmacology, 1999, 126, 673-680.
Aoki, "A study of endotoxemia in ulcerative colitis and Crohn's disease. I. Clinical Study," Acta Med Okayama, 32:147-58 (1978) abstract only.
Atreya et al. "Blockade of interleukin 6 trans signaling suppresses T-cell resistance against apoptosis in chronic intestinal inflammation: Evidence in Crohn disease and experimental colitis in vivo," Nat Med 6:583-8 (2000).
Bavaresco et al., "Stilbene compounds: from the grapevine to wine," Drugs Exp Clin Res 25:57-63 (1999) abstract only.
Davidson et al., "T helper cell 1-type CD4+T cells, but not B cells, mediate colitis in interleukin 10-deficient mice," J Exp Med 184:241-51 (1996).
Decker et al., "Interactions of α- and γ-interferon in the transcriptional regulation of the gene encoding a guanylate-binding protein," EMBO J 8:2009-2014 (1989).
Dustin et al., "Induction by IL 1 and interferon-γ: Tissue distribution, biochemistry, and function of a natural adherence molecule (ICAM-1)," J Immunol 137:245-54 (1986).
Geahlen et al., "Piceatannol (3,4,3',5'-tetrahydroxy-trans-stilbene) is a naturally occurring protein-tyrosine kinase inhibitor," BBRC, 165:241-5 (1989).
Goldberg et al., "Direct injection gas chromatographic mass spectrometric assay for *trans*-resveratrol," Anal Chem 66:3959-63 (1994).
Grimm et al., "Evidence for a CD14+population of monocytes in inflammatory bowel disease mucosa—implications for pathogenesis," Clin Exp Immunol 100:291-7 (1995).
Groux et al., "A CD4+T-cell subset inhibits antigen-specific T-cell responses and prevents colitis," Nature 389:737-42 (1997).
Hassel et al., "A dominant negative mutant of 2-5A-dependent Rnase suppresses antiproliferative and antiviral effects of interferon," EMBO 12:3297-3304 (1993).
Jeandet et al., "The production of resveratrol (3,5,4'-trihydroxystilbene) by grape berries in different developmental stages," Am J Enol Vitic, 42:41-6 (1991).
Jong et al., "Development of chronic colitis is dependent on the cytokine MIF," Nature Immunology 2:1061-1066 (2001).
Kageura et al., "Inhibitors from Rhubarb on lipopolysaccharide-induced nitric oxide production in macrophages: structural requirements of stilbenes for the activity," Bioorg Med Chem 9:1887-93 (2001).
Karaghiosoff et al., "Partial impairment of cytokine responses in Tyk2-deficient mice," Immunity 13:549-60 (2000).
Katze et al., "Functional expression and rna binding analysis of the inferon-induced, double-stranded RNA-activated, $68,000$-$M_r$ protein kinase in a cell-free system," Mol Cell Biol, 11:5497-5505 (1991).
Kawachi et al., "E-selectin expression in a murine model of chronic colitis," BBRC 268:547-52 (2000).
Ko et al., "Anti-platelet aggregation activity of stilbene derivatives from *Rheum undulatum*," Arch Pharm Res, 22:401-3 (1999) abstract only.
Kopp et al., "The Toll-receptor family and control of innate immunity," Curr Opin Immunol, 11:13-8 (1999).

(Continued)

*Primary Examiner* — Shaojia Anna Jiang
*Assistant Examiner* — Ganapathy Krishnan
(74) *Attorney, Agent, or Firm* — Medlen & Carroll, LLP

(57) ABSTRACT

The invention provides compositions and methods for reducing one or more symptoms of an autoimmune disease, inflammatory disease, and/or transplant rejection, by the administration to a subject in need thereof a pharmaceutically effective amount of a purified compound of any one of Formulae A-E. The invention's methods are useful for the prevention, amelioration, and treatment of autoimmune disease, inflammatory disease, and/or transplant rejection.

6 Claims, 11 Drawing Sheets

OTHER PUBLICATIONS

Kucharzik et al., "Circulating antiinflammatory cytokine IL-10 in patients with inflammatory bowel disease (IBD)," Clin Exp Immunol 100:452-6 (1995).
Lafaille et al., "High incidence of spontaneous autoimmune encephalomyelitis in immunodeficient anti-myelin basic protein T cell receptor transgenic mice," Cell 78:399-408 (1994).
Langcake et al., "The production of resveratrol by *Vitis vinifera* and other members of the vitaceae as a response to infection and injury," Physiol Plant Pathol, 9:77-86 (1976) not provided at this time.
Larner et al., "Transcriptional induction of two genes in human cells by β interferon," Proc Natl Acad Sci USA 81:6733-6737 (1984).
Levy et al., "Interferon-stimulated transcription: Isolation of an inducible gene and identification of its regulatory region," Proc Natl Acad Sci USA 83:8929-8933 (1986.
Lin et al., "Virus-dependent phosphorylation of the IRF-3 transcription factor regulates nuclear translocation, transactivation potential, and proteosome-mediated degradation," Mol Cell Biol 18:2986-96 (1998).
Loh et al., "Dissection of the interferon-γ MHC class II signal transduction pathway reveals that type I and type II interferon systems share common signaling component(s)," EMBO 11:1351-1363 (1992).
Luster et al., "Genomic characterization of a gamma-interferon-inducible gene (*ip-10*) and identification of an interferon-inducible hypersensitive site," Mol Cell Biol 7:3723-3731 (1987).
Madsen et al., "Inflammatory bowel disease: Lessons from the *IL-10* gene-deficient mouse," Clin Invest Med 24:250-7 (2001).
Marotta et al., "Induction of LFA-1/CD11a and ICAM-1/CD54 adhesion molecules on neoplastic B cells during in vivo treatment of chronic lymphocytic leukemia with interferon-$\alpha_2$," Blood 81:267-9 (1993).
Moreno-Manas et al., "Dehydroacetic acid chemistry. A new synthesis of resveratrol, a phytoalexin of *Vitis vinifera*," Anal Quim 81:157-161 (1985) not provided at this time.
Murakami et al., "Effect of stilbene derivatives on gastric $H^+$, $K^+$-ATPase," Biochem Pharmacol 44:1947-51 (1992).
Navarro et al., "Cytomegalovirus activates interferon immediate-early response gene expression and an interferon regulatory factor 3-containing interferon-stimulated response element-binding complex," Mol Cell Biol, 18:3796-3802 (1998).
Navarro and David, "p38-dependent activation of interferon regulatory factor 3 by lipopolysaccharide," J Biol Chem 274:35535-8 (1999).
Neurath et al., "Antibodies to interleukin-12 abrogate established experimental colitis in mice," J Exp Med 182:1281-90 (1995).
Palmieri et al., "Effect of resveratrol and some other natural compounds on tyrosine kinase activity and on cytolysis," Drugs Exp Clin Res 25:79-85 (1999) abstract only.
Porter et al., "Interferon response element of the human gene 6-16," EMBO J 7:85-92 (1988).
Raventos et al., "Direct HPLC analysis of *cis*- and *trans*-resveratrol and piceid isomers in Spanish red *Vitis vinifera* wines," J Agric Food Chem, 43:281-283 (1995).
Reich et al., "Interferon-induced transcription of a gene encoding a 15-kDa protein depends on an upstream enhancer element," Proc Natl Acad Sci USA 84:6394-6398 (1987).
Schreiber et al., "Immunoregulatory role of interleukin 10 in patients with inflammatory bowel disease," Gastroenterology 108:1434-44 (1995).
Sevransky et al., "Tyrphostin AG556 improves survival and reduces multiorgan failure in canine *Escherichi coli* peritonitis," J Clin Invest 99:1966-1973 (1997).
Su and David, "Distinct mechanisms of STAT phosphorylation via the interferon-⁻receptor," J Biol Chem 275:12661-6 (2000).
Thakkar et al., Synthesis and protein-tyrosine kinase inhibitory activity of polyhydroxylated stilbene analogues of piceatannol, J Med Chem, 36:2950-5 (1993).

van Dullemen et al., "Treatment of Crohn's disease with anti-tumor necrosis factor chimeric monoclonal antibody (cA2)," Gastroenterology 109:129-35 (1995).
Waffo Teguo et al., "Isolation, identification, and antioxidant activity of three stilbene glucosides newly extracted from *Vitis vinifera* cell cultures," J Nat Prod 61:655-7 (1998).
Wathelet et al., "Virus infection induces the assembly of coordinately activated transcription factors on the IFN-β enhancer in vivo," Molecular Cell 1:507-518 (1998).
Yoneyama et al., "Direct triggering of the type I interferon system by virus infection: activation of a transcription factor complex containing IRF-3 and CBP/p300," EMBO J 17:1087-1095 (1998).
Zhou et al., "Expression cloning of 2-5A-dependent RNAase: A uniquely regulated mediator of interferon action," Cell, 72:753-765 (1993).
Abu-Lawi et al., "Induction of serine and threonine protein phosphorylation by endotoxin-associated protein in murine resident peritoneal macrophages," Infect Immun, 63:498-502 (1995).
Amura et al., Mechanisms involved in the pathogenesis of sepsis are not necessarily reflected by in vitro cell activation studies, Infect Immun, 66:5372-5378 (1998).
Brenner et al., "Suppression of experimental autoimmune encephalomyelitis by tyrphostin AG-556," Exp Neurol, 154:489-98 (1998).
Brumbaugh et al., "Functional role for Syk tyrosine kinase in natural killer cell-mediated natural cytotoxicity,"0 J Exp Med, 186:1965-74 (1997).
Cochran et al., "The effect of a tyrosine kinase inhibitor on endotoxin mortality and splenocyte mediator production in the neonatal rat," Shock, 11:35-8 (1999) abstract only.
Constantin et al., "Tyrphostin AG490, a tyrosine kinase inhibitor, blocks actively induced experimental autoimmune encephalomyelitis," Eur J Immunol, 28:3523-9 (1998).
Cuzzocrea et al., "The tyrosine kinase inhibitor tyrphostin AG 126 reduced the development of colitis in the rat," Lab Invest, 80:1439-53 (2000).
Galea et al., "Differential suppression of glial nitric oxide synthase induction by structurally related tyrosine kinase inhibitors," Neurosci Lett, 200:195-8 (1995).
Gill et al., "3,3',5'-Tri-O-methylpiceatannol and 4,3',5'-tri-O-methylpiceatannol: improvements over piceatannol in bioactivity," J Nat Prod, 50:36-40 (1987).
Jarrar et al., "Inhibition of tyrosine kinase signaling after trauma-hemorrhage: a novel approach for improving organ function and decreasing susceptibility to subsequent sepsis," Ann Surg, 231:399-407 (2000).
Kong et al., "Protein tyrosine kinase inhibitors suppress the production of nitric oxide in mixed glia, microglia-enriched or astrocyte-enriched cultures," Brain Res 729:102-9 (1996).
Levitzki et al., "Tyrosine kinase inhibition: an approach to drug development," Science, 267:1782-8 (1995).
Levitzki "Protein tyrosine kinase inhibitors as novel therapeutic agents," Pharmacol Ther, 82:231-9 (1999).
Matsuda et al., "Effects of stilbene constituents from rhubarb on nitric oxide production in lipopolysaccharide-activated macrophages," Bioorg Med Chem Lett, 10:323-7 (2000).
Novogrodskey "Prevention of lipopolysaccharide-induced lethal toxicity by tyrosine kinase inhibitors," Science, 264:1319-22 (1994).
Ogura et al., "Protective effect of tyrphostin AG-556 on shock induced by endotoxin or gram positive bacteria," Shock 12:105-10 (1999) abstract only.
Tsai et al., "Suppression of nitric oxide synthase and the down-regulation of the activation of NFkappaB in macrophages by resveratrol," Br J Pharmacol, 126:673-80 (1999).
Vanichkin et al., "Late administration of a lipophilic tyrosine kinase inhibitor prevents lipopolysaccharide and *Escherichia coli*-induced lethal toxicity," J Infect Dis, 173:927-33 (1996).

* cited by examiner

METHODS AND COMPOSITIONS FOR PREVENTION AND TREATMENT OF INFLAMMATORY DISEASE, AUTOIMMUNE DISEASE AND TRANSPLANT REJECTION

This application is a continuation of, and claims priority to, U.S. patent application Ser. No. 12/843,410, filed Jul. 26, 2010, now U.S. Pat. No. 8,080,527, which is a continuation of U.S. patent application Ser. No. 10/494,452, filed Apr. 30, 2004, which issued as U.S. Pat. No. 7,811,996 on Oct. 12, 2010 and which is the U.S. national stage filing of PCT Application No. PCT/US2002/035153, filed Nov. 1, 2002, now abandoned, which claims priority to U.S. Provisional Application Ser. No. 60/336,759 to Michael David, filed Nov. 2, 2001, now abandoned, the contents of which are incorporated herein in their entirety.

This invention was made with government support under AI 47182 awarded by the National Institutes of Health. The government has certain rights in the invention.

FIELD OF THE INVENTION

The invention relates to compositions and methods for reducing one or more symptoms of an autoimmune disease, inflammatory disease, and/or transplant rejection, by the administration to a subject in need thereof a pharmaceutically effective amount of a purified compound of any one of Formulae A-E. The invention's methods are useful for the prevention, amelioration, and treatment of autoimmune disease, inflammatory disease, and/or transplant rejection.

BACKGROUND OF THE INVENTION

Inflammatory disease, autoimmune disease, and transplant rejection exert a devastating personal and economic burden. Inflammatory disease occurs when an inflammatory response is initiated that is inappropriate and/or does not resolve in the normal manner but rather persists and results in a chronic inflammatory state. Examples of some of the most common and problematic inflammatory diseases are sepsis, septic shock, rheumatoid arthritis, inflammatory bowel disease (IBD), psoriasis, asthma, emphysema, colitis and ischemia-reperfusion injury. In particular, sepsis, which is a systemic inflammatory response to infection, leads to multi-organ failure through disseminated intravascular coagulation (DIC). In this disease, auto amplification processes contribute to the increased acceleration of coagulation abnormalities, inflammation, and endothelial injury. Sepsis leads to approximately 700,000 hospitalizations, of which 45% progress to septic shock leading to 100,000 lethalities, which makes septic shock the tenth leading cause of death in the U.S.A.

Several approaches have been tried to control sepsis including anti-LPS antiserum, anti-CD14 antiserum, anti-TNFα antiserum or soluble TNFα receptor, anti-IL1 antiserum or IL1-R antagonist, PAF antagonist, IL-10, tissue factor pathway inhibitors, glucocorticoids, nonsteroidal anti-inflammatory drugs (NSAIDs), and nitrogen oxide (NO) inhibitors. However, none of these approaches has provided significant beneficial outcomes in human clinical trials if sepsis.

Autoimmune disease is exemplified by inflammatory bowel disease, which is a widespread and devastating autoimmune syndrome that encompasses Inflammatory Bowel Syndrome (IBS), Crohn's Disease and Chronic Ulcerative Colitis. Inflammatory bowel disease/Crohn's disease represent autoimmune disorders (Groux, et al. (1997) Nature 389, no. 6652:737-42; Davidson, et al. (1996) J Exp Med 184, no. 1:241-51) that are additionally characterized by significant endotoxin levels in the blood, which promote further lymphocyte and macrophage activation (Aoki (1978) Acta Med Okayama 32, no. 2:147-58; Grimm, et al. (1995) Clin Exp Immunol 100, no. 2:291-7). Crohn's disease is a serious inflammatory disease of the gastrointestinal (GI) tract that behaves similarly to ulcerative colitis, from which it may be difficult to differentiate. Crohn's disease predominates in the intestine (ileum) and the large intestine (colon), but may occur in any section of the GI tract. Unlike Crohn's disease, in which all layers of the intestine are involved, and in which there can be normal healthy bowel in between patches of diseased bowel, ulcerative colitis affects the innermost lining (mucosa) of the colon in a continuous manner.

400,000 Americans have Crohn's disease, and over 1 million people suffer from general inflammatory bowel syndrome (IBS). Currently, therapy for IBDs is mostly restricted to treatment that decreases inflammation and usually controls the symptoms, but does not provide a cure.

Another example of autoimmune disease is rheumatoid arthritis (RA). RA is the most common form of inflammatory arthritis, is a disorder of unknown etiology which affects 1% of the adult population, and is characterized by symmetric, chronic, erosive synovitis (inflammation of the joint synovial lining) and frequent multisystem involvement. Most patients exhibit a chronic fluctuating course of disease that, if left untreated, results in progressive joint destruction, deformity, disability, and premature death. Symptoms indicative of RA include pain and swelling of the joints (usually symmetrical), morning stiffness of joints and muscles, general weakness/fatigue and fever and weight loss. RA results in more than 9 million physician visits and more than 250,000 hospitalizations per year in the U.S. each year. It frequently affects patients in their most productive years, and thus, disability results in major economic loss.

At present, there is no cure or prevention (prophylactic) available for rheumatoid arthritis, but only regimes that address symptoms such as pain and stiffness. The five major treatment modalities for this disease include medication (pharmacological), physical (exercise), joint protection, lifestyle changes, and surgery. Therapeutics for rheumatoid arthritis can be divided into three groups: NSAIDs, disease modifying anti-rheumatic drugs (DMARDs) also known as second line agents, and corticosteroids. Each of these therapeutics has drawbacks.

For example, although NSAIDs effectively address the acute inflammatory component of rheumatoid arthritis, they only treat its symptoms, and do not change the progression of the underlying disease. The deleterious side effects of NSAIDs can be serious with prolonged administration and are mainly gastrointestinal (heartburn, bleeding or ulcers).

DMARDs work by suppressing immune cells involved in the inflammatory response thus slowing progression of the disease. However, they are unable to reverse permanent joint damage. The most common drugs of this class are gold salts, methotrexate, azathioprine, sulphasalazine, hydroxychloroquine, penicillamine and chloroquine. DMARDs often take several weeks for beneficial effects to be seen and in many cases the exact mode of efficacy in rheumatoid arthritis is unknown. Side effects are numerous including mouth sores, rashes, diarrhea and nausea. More serious side effects which necessitate careful monitoring through regular blood and urine tests include liver and kidney damage, excessive lowering of the white blood cell count (immune suppression) and platelet count (blood clotting).

The long term-use of corticosteroids poses serious side effects including cataracts, high blood pressure, muscle wasting, bruising, thinning of skin and bones, weight gain, diabetes and susceptibility to infection. Thus, none of the therapeutic approaches to RA are satisfactory.

Successful organ transplantation requires effective physiological and pharmacological intervention of the immune system of an organ recipient. Immunologic mechanisms are universal among the human species. But histocompatibility variations between donor and recipient lead inevitably to rejection of donor tissue by stimulation of the recipient's immune system except, perhaps, in donor-recipient pairing of the monozygotic type. One approach to intervention in the immune response in an organ transplant recipient, especially a recipient targeted for an allogenic or homologous graft, is by the use of immunosuppressive drugs. These drugs have been used to prolong survival of transplanted organs in recipients in cases involving, for example, transplants of kidney, liver, heart, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation. These drugs, however, have many drawbacks.

For example, antiproliferative agents (e.g., azathioprine, cyclophosphamide and methotrexate) mediate mitosis and cell division. However, these agents have severe side effects on normal cell populations which have a high turn-over rate, such as bone marrow cells and cells of the gastrointestinal (GI) tract lining. Accordingly, such drugs often have severe side effects, particularly, bone marrow depression, liver damage, hair loss and GI tract disturbances.

A second class of immunosuppressive drugs for use in transplantation is provided by compounds having antiinflammatory action, such as adrenal corticosteroids (e.g., prednisone and prednisolone). However, adrenal corticosteroids lack specificity of effect and can exert a broad range of metabolic, antiinflammatory and auto-immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds which generally prevent or inhibit lymphocyte activation, for example, cyclosporins. Cyclosporins have several significant disadvantages. Firstly, cyclosporins are non-specific immunosuppressive. Thus, immunologic reactions to transplanted tissue are not totally impeded, and desirable immune reactions may be reduced against other foreign antigens. Secondly, cyclosporins can produce severe side effects in many organ recipients. In addition, cyclosporins show host-variable effects on the liver, the CNS and GI tract. Significant among the adverse side effects are damage to the kidney and hyperplasia of gum tissue.

Thus, there remains a need for compositions and methods for the prevention and treatment of inflammatory disease, autoimmune disease, and transplant rejection.

SUMMARY OF THE INVENTION

The invention provides compositions and methods for the prevention and treatment of inflammatory disease, autoimmune disease, and transplant rejection. In one embodiment, the invention provides a method for reducing one or more symptoms of a condition selected from autoimmune disease, inflammatory disease, and transplant rejection, said method comprising administering to a subject a pharmaceutically effective amount of a purified compound having the following structure of Formula A,

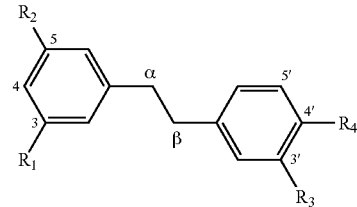

wherein: (a) each of $R_1$, $R_2$, $R_3$ and $R_4$ is independently selected from hydrido, hydroxy, alkoxyl having from 1 to 4 carbon atoms, pyranose sugar, and furanose sugar, (b) each of $\alpha$ and $\beta$ is from 1 to 5 atoms independently selected from one or more of oxygen, carbon, sulfur, nitrogen, and phosphorus, wherein said oxygen, carbon, sulfur, nitrogen, and phosphorus atoms are linked to each other by one or more single bonds or one or more double bonds, and wherein each of said oxygen, carbon, sulfur, nitrogen, and phosphorus atoms is optionally further linked to a hydrido or hydroxyl, and (c) the carbon atom at position 4, position 5', or positions 4 and 5' is covalently linked to a hydrido, hydroxy, alkoxyl having from 1 to 4 carbon atoms, pyranose sugar, or furanose sugar, thereby reducing one or more symptoms of said condition. In one preferred embodiment, each of $\alpha$ and $\beta$ is —CH—, preferably, each of $R_1$ and $R_2$ is —OH, and alternatively, each of $R_1$ and $R_2$ is independently selected from —OCH$_3$ and —OCH$_2$—CH$_3$, while more preferably, each of $R_1$ and $R_2$ is —OCH$_3$. Alternatively, each of $R_1$, $R_2$, $R_3$, and $R_4$ is —OH, and the compound is piceatannol. In another alternative, one or more of $R_1$, $R_2$, $R_3$, and $R_4$ is —OCH$_3$, preferably, wherein each of $R_1$, $R_2$, $R_3$, and $R_4$ is —OCH$_3$, and the compound is tetramethoxy-stilbene. In a further alternative, one or more of $R_1$, $R_2$, $R_3$, and $R_4$ is —OCH$_2$—CH$_3$, more preferably, each of $R_1$, $R_2$, $R_3$, and $R_4$ is —OCH$_2$—CH$_3$, and the compound is tetraethoxy-stilbene. Alternatively, each of $R_1$, $R_2$, and $R_4$ is —OH, $R_3$ is —H, and the compound is resveratrol. In a further alternative, one or more of $R_1$, $R_2$, and $R_4$ is —OCH$_3$, and $R_3$ is —H, more preferably, each of $R_1$, $R_2$, and $R_4$ is —OCH$_3$, $R_3$ is —H, and the compound is trimethoxy-stilbene. In another alternative, one or more of $R_1$, $R_2$, and $R_4$ is —OCH$_2$—CH$_3$, and $R_3$ is —H, more preferably each of $R_1$, $R_2$, and $R_4$ is —OCH$_2$—CH$_3$, and $R_3$ is —H. In yet another alternative, each of $R_1$, $R_2$, and $R_3$ is —OH, $R_4$ is —OCH$_3$, and the compound is rhapontigenin. In another embodiment, the compound is piceatannol, tetramethoxy-piceatannol, resveratrol, or rhapontigenin.

The invention further provides a method for reducing one or more symptoms of a condition selected from sepsis, inflammatory bowel disease, multiple sclerosis, and asthma, said method comprising administering to a subject a pharmaceutically effective amount of a purified compound having the following structure of Formula A,

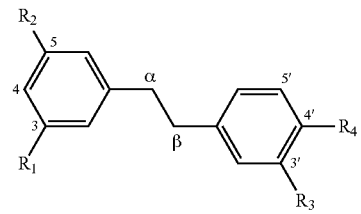

wherein: (a) each of $R_1$, $R_2$, $R_3$ and $R_4$ is independently selected from hydrido, hydroxy, alkoxyl having from 1 to 4 carbon atoms, pyranose sugar, and furanose sugar, (b) each of α and β is from 1 to 5 atoms independently selected from one or more of oxygen, carbon, sulfur, nitrogen, and phosphorus, wherein said oxygen, carbon, sulfur, nitrogen, and phosphorus atoms are linked to each other by one or more single bonds or one or more double bonds, and wherein each of said oxygen, carbon, sulfur, nitrogen, and phosphorus atoms is optionally further linked to a hydrido or hydroxyl, and (c) the carbon atom at position 4, position 5', or positions 4 and 5' is covalently linked to a hydrido, hydroxy, alkoxyl having from 1 to 4 carbon atoms, pyranose sugar, or furanose sugar, thereby reducing one or more symptoms of sepsis. In one embodiment, the subject is human. In another embodiment, the subject is a mouse. In yet another embodiment, the subject is canine. In a preferred embodiment, the compound is piceatannol, tetramethoxy-piceatannol, or resveratrol. In one embodiment, administering is parenteral, oral, intraperitoneal, or intranasal. In another embodiment, administering is before manifestation of one or more symptoms of sepsis, concomitant with manifestation of one or more symptoms of sepsis, and/or after manifestation of one or more symptoms of sepsis.

Further provided by the invention is a method for reducing one or more symptoms of a condition selected from an autoimmune disease, inflammatory disease, and transplant rejection, the method comprising administering to a subject a pharmaceutically effective amount of a purified compound having the following structure of Formula B

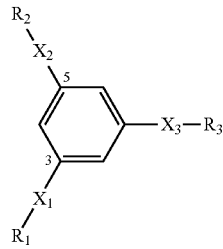

wherein: (a) $X_3$ is from 1 to 10 atoms independently selected from one or more of oxygen, carbon, sulfur, nitrogen, and phosphorus, and wherein the atoms are linked to each other by one or more single bonds or one or more double bonds, and wherein each of the atoms is optionally further linked to a hydrido or hydroxyl, (b) $R_3$ is selected from $(\text{---H})_x$ wherein x is selected from 1, 2 and 3, straight or branched chain alkyl having from 1 to 20 carbon atoms, cyclopentyl, cyclohexyl, benzyl, pyrane, furane, pyridine, pyrimidine, and a moiety having the following structure of Formula C,

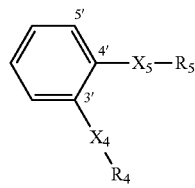

(c) each of $X_1$, $X_2$, $X_4$, and $X_5$ is independently selected from hydrogen, hydroxyl, and an alkoxyl having from 1 to 10 carbon atoms, (d) each of $R_1$, $R_2$, $R_4$ and $R_5$ is independently selected from hydrogen, alkyl having from 1 to 20 carbon atoms, pyranose sugar, and furanose sugar, and (e) the carbon atom at position 4 of Formula B, position 5' of Formula C, or position 4 of Formula B and position 5' of Formula C is covalently linked to a hydrido, hydroxy, alkoxyl having from 1 to 4 carbon atoms, pyranose sugar, or furanose sugar, thereby reducing one or more symptoms of the condition. In one preferred embodiment, each of $R_1$, $R_2$, $R_4$, and $R_5$ is selected from ---H, ---CH$_3$, and ---C$_2$H$_5$. Alternatively, $X_3$ is selected from ---C≡C--- and ---CH═CH---. In another alternative, $R_1$, $R_2$, $R_4$, and $R_5$ is an alkyl having from 1 to 4 carbon atoms. In a further alternative, $R_1$, $R_2$, $R_4$, and $R_5$ is an alkyl having one carbon atom. In yet another alternative, the purified compound has the following structure of Formula A,

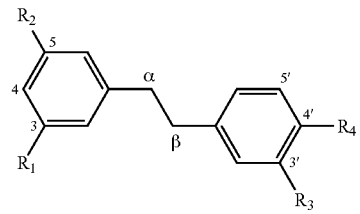

wherein: (a) each of $R_1$, $R_2$, $R_3$ and $R_4$ is independently selected from hydrido, hydroxy, alkoxyl having from 1 to 4 carbon atoms, pyranose sugar, and furanose sugar, (b) each of α and β is from 1 to 5 atoms independently selected from one or more of oxygen, carbon, sulfur, nitrogen, and phosphorus, wherein the oxygen, carbon, sulfur, nitrogen, and phosphorus atoms are linked to each other by one or more single bonds or one or more double bonds, and wherein each of the oxygen, carbon, sulfur, nitrogen, and phosphorus atoms is optionally further linked to a hydrido or hydroxyl, and (c) the carbon atom at position 4, position 5', or positions 4 and 5' is covalently linked to a hydrido, hydroxy, alkoxyl having from 1 to 4 carbon atoms, pyranose sugar, or furanose sugar.

Additionally provided herein is a method for reducing one or more symptoms of a condition selected from an autoimmune disease, inflammatory disease, and transplant rejection, the method comprising administering to a subject a pharmaceutically effective amount of a purified compound having the following structure of Formula D

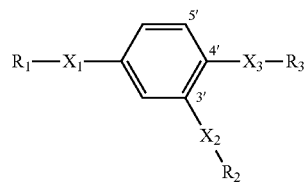

wherein: (a) $X_1$ is from 1 to 10 atoms independently selected from one or more of oxygen, carbon, sulfur, nitrogen, and phosphorus, and wherein the atoms are linked to each other by one or more single bonds or one or more double bonds, and wherein each of the oxygen, carbon, sulfur, nitrogen, and phosphorus atoms is optionally further linked to a hydrido or hydroxyl, (b) $R_1$ is selected from $(\text{---H})_x$ wherein x is selected from 1, 2 and 3, straight or branched chain alkyl having from 1 to 20 carbon atoms, cyclopentyl, cyclohexyl, benzyl, pyrane, furane, pyridine, pyrimidine, and a moiety having the following structure of Formula E

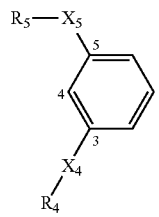

(d) each of $X_2$, $X_3$, $X_4$, and $X_5$ is independently selected from hydrogen, oxygen, alkyl having from 1 to 4 carbon atoms, alkoxyl having from 1 to 4 carbon atoms, $SY_2$, $NY_2$, and $PY_2$ wherein Y is independently selected from —H and —OH, (h) each of $R_2$, $R_3$, $R_4$ and $R_5$ is independently selected from $(—H)_x$ wherein x is selected from 1, 2 and 3, an alkyl having from 1 to 20 carbon atoms, pyranose sugar, and furanose sugar, and (i) the carbon atom at position 5' of Formula D, position 4 of Formula E, or position 5' of Formula D and position 4 of Formula E is covalently linked to a hydrido, hydroxy, alkoxyl having from 1 to 4 carbon atoms, pyranose sugar, or furanose sugar, thereby reducing one or more symptoms of the condition. In one preferred embodiment, the purified compound has following structure of Formula A,

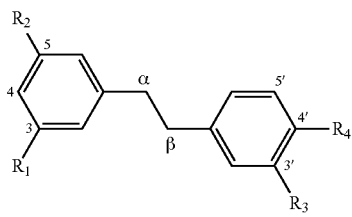

wherein: (a) each of $R_1$, $R_2$, $R_3$ and $R_4$ is independently selected from hydrido, hydroxy, alkoxyl having from 1 to 4 carbon atoms, pyranose sugar, and furanose sugar, (b) each of α and β is from 1 to 5 atoms independently selected from one or more of oxygen, carbon, sulfur, nitrogen, and phosphorus, wherein the oxygen, carbon, sulfur, nitrogen, and phosphorus atoms are linked to each other by one or more single bonds or one or more double bonds, and wherein each of the oxygen, carbon, sulfur, nitrogen, and phosphorus atoms is optionally further linked to a hydrido or hydroxyl, and (c) the carbon atom at position 4, position 5', or positions 4 and 5' is covalently linked to a hydrido, hydroxy, alkoxyl having from 1 to 4 carbon atoms, pyranose sugar, or furanose sugar.

Further still, the invention provides a method for reducing one or more symptoms of an autoimmune disease, inflammatory disease, and/or transplant rejection, the method comprising administering to a subject in need thereof a pharmaceutically effective amount of a purified compound of Formula B

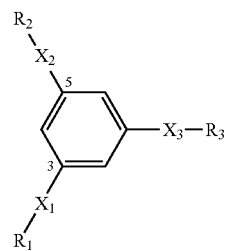

wherein: (a) $X_3$ is selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (b) $R_3$ is selected from $(—H)_x$, straight or branched chain alkyl having from 1 to 20 carbon atoms, cyclopentyl, cyclohexyl, benzyl, purane, furane, pyridine, pyrimidine, and Formula C,

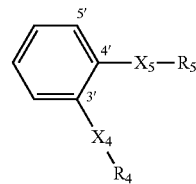

(c) x is selected from 1, 2 and 3, (d) each of $X_1$, $X_2$, $X_4$, and $X_5$ is independently selected from H, O, $CY_2$, $SY_2$, $NY_2$, and $PY_2$, (e) Y is independently selected from —H and —OH, (f) w is an integer from 1 to 10, (g) n is selected from 0, 1, 2, 3, and 4, and (h) each of $R_1$, $R_2$, $R_4$ and $R_5$ is independently selected from $(—H)_x$, and an alkyl having from 1 to 20 carbon atoms, and (i) the carbon atom at position 4 of Formula B, position 5' of Formula C, or position 4 of Formula B and position 5' of Formula C is covalently linked to a hydrido, hydroxy, alkoxyl having from 1 to 4 carbon atoms, pyranose sugar, or furanose sugar, glycosylated derivatives, salts, solvates, racemic mixtures, racemic-diastereomeric mixtures, tautomers and isomers thereof; thereby reducing one or more symptoms of the disease. While not intending to limit the number or nature of moieties in any of the Formulae in this invention, in one embodiment, w is an integer from 1 to 4, more preferably w is 2. In another embodiment, each of $X_1$ and $X_2$ is O. In an alternative embodiment, each of $R_1$, $R_2$, $R_4$, and $R_5$ is selected from —H, —$CH_3$, and —$C_2H_5$. In yet another embodiment, $X_3$ is selected from —C=C— and —CH—CH—. In yet a further embodiment, Y is —H. In yet another embodiment, the alkyl has from 1 to 4 carbon atoms, and more preferably the alkyl has one carbon atom. Alternatively, the alkyl is selected from hydrocarbyl, halocarbyl, and hydrohalocarbyl. Preferably, the halogen in the halocarbyl or hydrohalocarbyl is chlorine, bromine, or fluorine. In an alternative embodiment, the pyrane is selected from glucopyrane, mannopyrane, galactopyrane, and fructopyrane. In another alternative embodiment, the furane is selected from arabinofurane and ribofurane. In a particularly preferred embodiment, the purified compound has Formula A,

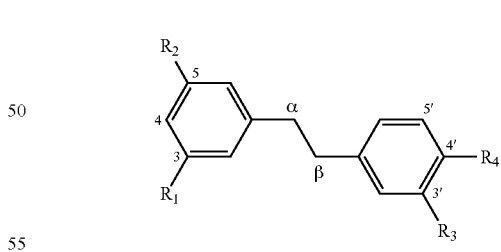

wherein: (a) each of $R_1$ and $R_2$ is independently selected from —OH and —O$(CH_2)_n$—$CH_3$, (b) each of $R_3$ and $R_4$ is independently selected from —H, —OH, and —O$(CH_2)_n$—$CH_3$, (c) each of α and β is independently selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (d) n is selected from 0, 1, 2, 3, and 4, and (e) w is selected from 1, 2, 3, and 4, and (e) the carbon atom at position 4, position 5', or positions 4 and 5' is covalently linked to a hydrido, hydroxy, alkoxyl having from 1 to 4 carbon atoms, pyranose sugar, or furanose sugar, The invention further provides a method for reducing one or more symptoms of an autoimmune disease, inflammatory disease, and/or transplant rejection, the method comprising administering to a subject in need thereof a pharmaceutically effective amount of a purified compound of Formula D,

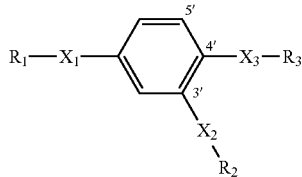

wherein: (a) $X_1$ is selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (b) $R_1$ is selected from $(—H)_x$, straight or branched chain alkyl having from 1 to 20 carbon atoms, cyclopentyl, cyclohexyl, benzyl, purane, furane, pyridine, pyrimidine, and Formula E,

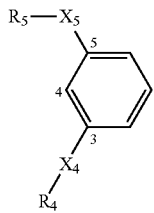

(c) x is selected from 1, 2 and 3, (d) each of $X_2$, $X_3$, $X_4$, and $X_5$ is independently selected from H, O, $CY_2$, $SY_2$, $NY_2$, and $PY_2$, (e) Y is independently selected from —H and —OH, (f) w is an integer from 1 to 10, (g) n is selected from 0, 1, 2, 3, and 4, and (h) each of $R_2$, $R_3$, $R_4$ and $R_5$ is independently selected from $(—H)_x$ and an alkyl having from 1 to 20 carbon atoms, and (i) the carbon atom at position 5' of Formula D, position 4 of Formula E, or position 5' of Formula D and position 4 of Formula E is covalently linked to a hydrido, hydroxy, alkoxyl having from 1 to 4 carbon atoms, pyranose sugar, or furanose sugar, glycosylated derivatives, salts, solvates, racemic mixtures, racemic-diastereomeric mixtures, tautomers and isomers thereof, thereby reducing one or more symptoms of the disease. While not intending to limit the number or nature of moieties in any of the Formulae in this invention, in one embodiment, w is an integer from 1 to 4, more preferably, w is 2. In another embodiment, each of $X_4$ and $X_5$ is O. In yet another embodiment, each of $R_2$, $R_3$, $R_4$, and $R_5$ is selected from —H, —$CH_3$, and —$C_2H_5$. In a further embodiment, $X_1$ is selected from —C=C— and —CH—CH—. In an alternative embodiment, Y is —H. In yet another embodiment, the alkyl has from 1 to 4 carbon atoms, and more preferably, one carbon atom. Alternatively, the alkyl is hydrocarbyl, halocarbyl, or hydrohalocarbyl. In a preferred embodiment, the halogen in the halocarbyl or hydrohalocarbyl is chlorine, bromine, or fluorine. In an alternative embodiment, the pyrane is glucopyrane, mannopyrane, galactopyrane, or fructopyrane. In yet another embodiment, the furane is arabinofurane or ribofurane. In a most preferred embodiment, the purified compound has Formula A,

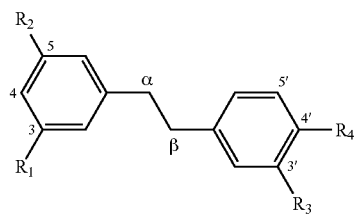

wherein: (a) each of $R_1$ and $R_2$ is independently selected from —OH and —$O(CH_2)_n$—$CH_3$, (b) each of $R_3$ and $R_4$ is independently selected from —H, —OH, and —$O(CH_2)_n$—$CH_3$, (c) each of α and β is independently selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (d) n is selected from 0, 1, 2, 3, and 4, and (e) w is selected from 1, 2, 3, and 4, and (e) the carbon atom at position 4, position 5', or positions 4 and 5' is covalently linked to a hydrido, hydroxy, alkoxyl having from 1 to 4 carbon atoms, pyranose sugar, or furanose sugar, The invention additionally provides a method for reducing one or more symptoms of an autoimmune disease, inflammatory disease, and/or transplant rejection, the method comprising administering to a subject in need thereof a pharmaceutically effective amount of a purified compound of Formula A,

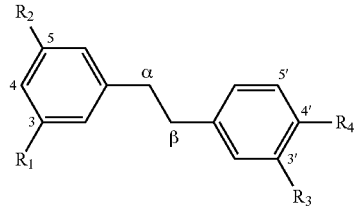

wherein: (a) each of $R_1$ and $R_2$ is independently selected from —OH and —$O(CH_2)_n$—$CH_3$, (b) each of $R_3$ and $R_4$ is independently selected from —H, —OH, and —$O(CH_2)_n$—$CH_3$, (c) each of α and β is independently selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (d) n is selected from 0, 1, 2, 3, and 4, (e) w is selected from 1, 2, 3, and 4, and (e) the carbon atom at position 4, position 5', or positions 4 and 5' is covalently linked to a hydrido, hydroxy, alkoxyl having from 1 to 4 carbon atoms, pyranose sugar, or furanose sugar, glycosylated derivatives, salts, solvates, racemic mixtures, racemic-diastereomeric mixtures, tautomers and isomers thereof, thereby reducing one or more symptoms of the disease. In a preferred embodiment, each of α and β is —CH—. More preferably, each of $R_1$ and $R_2$ is —OH, or each of $R_1$ and $R_2$ is independently selected from —$OCH_3$ and —$OCH_2$—$CH_3$, yet more preferably, each of $R_1$ and $R_2$ is —$OCH_3$. In an alternative embodiment, each of $R_1$, $R_2$, $R_3$, and $R_4$ is —OH, and the compound is piceatannol. In a further alternative embodiment, one or more of $R_1$, $R_2$, $R_3$, and $R_4$ is —$OCH_3$. In a more preferred embodiment, each of $R_1$, $R_2$, $R_3$, and $R_4$ is —$OCH_3$, and the compound is tetramethoxy-stilbene. In yet another embodiment, one or more of $R_1$, $R_2$, $R_3$, and $R_4$ is —$OCH_2$—$CH_3$, and more preferably, each of $R_1$, $R_2$, $R_3$, and $R_4$ is —$OCH_2$—$CH_3$, and the compound is tetraethoxy-stilbene. In another alternative, each of $R_1$, $R_2$, and $R_4$ is —OH, $R_3$ is —H, and the compound is resveratrol. A further embodiment is that one or more of $R_1$, $R_2$, and $R_4$ is —$OCH_3$, and $R_3$ is —H, and more preferably, each of $R_1$, $R_2$, and $R_4$ is —$OCH_3$, $R_3$ is —H, and the compound is trimethoxy-stilbene. Alternatively, one or more of $R_1$, $R_2$, and $R_4$ is —$OCH_2$—$CH_3$, and $R_3$ is —H, more preferably, each of $R_1$, $R_2$, and $R_4$ is —$OCH_2$—$CH_3$, and $R_3$ is —H. As an additional alternative, each of $R_1$, $R_2$, and $R_3$ is —OH, $R_4$ is —$OCH_3$, and the compound is rhapontigenin. Most preferably, compound is piceatannol, tetramethoxy-piceatannol, resveratrol, or rhapontigenin.

While not necessary, it is advantageous that the invention's compounds be glycosylated. In one embodiment for Formula A, $R_1$ is glycosylated to a pyranose sugar or a furanose sugar. Preferably, the pyranose sugar is glucopyranose, mannopyranose, galactopyranose, or fructopyranose. Alternatively, the furanose sugar is arabinofuranose or ribofuranose. In another alternative, the sugar is esterified to a galloyl moiety. More preferably, the ester is a 2"-O-gallate ester or a 6"-O-gallate ester.

Also provided herein is a method for reducing one or more symptoms of an autoimmune disease, inflammatory disease, and/or transplant rejection, the method comprising administering to a subject in need thereof a pharmaceutically effective amount of a purified compound of Formula A,

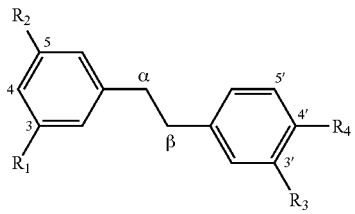

wherein: (a) each of $R_1$ and $R_2$ is independently selected from —H, —OH and —$O(CH_2)_n$—$CH_3$, (b) each of $R_3$ and $R_4$ is independently selected from —OH and —$O(CH_2)_n$—$CH_3$, (c) each of α and β is independently selected from $O_n$, $(CY)_w$, $(CY_2)_w$, $(SY)_w$, $(SY_2)_w$, $(NY)_w$, $(NY_2)_w$, $(PY)_w$, and $(PY_2)_w$, (d) n is selected from 0, 1, 2, 3, and 4, (e) w is selected from 1, 2, 3, and 4, and (e) the carbon atom at position 4, position 5', or positions 4 and 5' is covalently linked to a hydrido, hydroxy, alkoxyl having from 1 to 4 carbon atoms, pyranose sugar, or furanose sugar, glycosylated derivatives, salts, solvates, racemic mixtures, racemic-diastereomeric mixtures, tautomers and isomers thereof, thereby reducing one or more symptoms of the disease. In one embodiment, each of α and β is —CH—. More preferably, each of $R_3$ and $R_4$ is —OH, and alternatively, each of $R_3$ and $R_4$ is independently selected from —$OCH_3$ and —$OCH_2$—$CH_3$, yet more preferably, each of $R_3$ and $R_4$ is —$CH_3$. In another embodiment, each of $R_1$, $R_2$, $R_3$, and $R_4$ is —OH, and the compound is piceatannol. In a further embodiment, one or more of $R_1$, $R_2$, $R_3$, and $R_4$ is —$OCH_3$, more preferably, each of $R_1$, $R_2$, $R_3$, and $R_4$ is —$OCH_3$, and the compound is tetramethoxy-stilbene. In yet another embodiment, one or more of $R_1$, $R_2$, $R_3$, and $R_4$ is —$OCH_2$—$CH_3$, and more preferably, each of $R_1$, $R_2$, $R_3$, and $R_4$ is —$OCH_2$—$CH_3$, and the compound is tetraethoxy-stilbene.

It is desirable, though not necessary, that Formula A be glycosylated, wherein $R_1$ is glycosylated to a pyranose sugar or a furanose sugar, preferably the pyranose sugar is glucopyranose, mannopyranose, galactopyranose, or fructopyranose, while the furanose sugar is arabinofuranose or ribofuranose. Alternatively, the sugar is esterified to a galloyl moiety, and preferably the ester is a 2"-O-gallate ester or is a 6"-O-gallate ester.

DEFINITIONS

Figure 1:
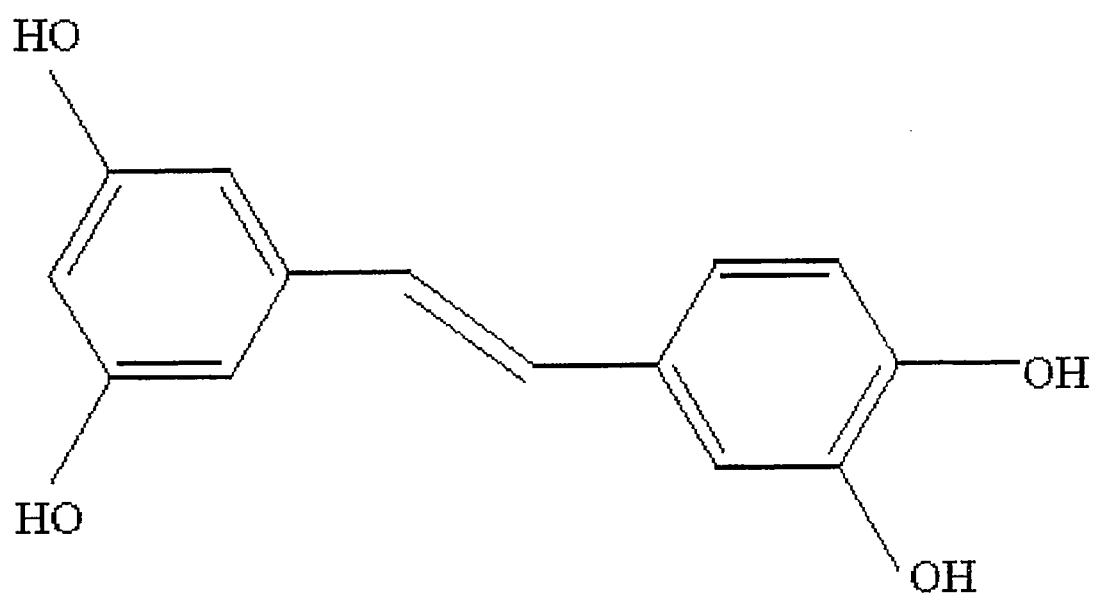
FIG. 1 shows piceatannol.

To facilitate understanding of the invention, a number of terms are defined below.

As used herein, the term "purified" refers to a compound that is removed from its natural environment, isolated, or separated. An "isolated" molecule is therefore a purified molecule. "Purified" molecules are at least 20% free, preferably at least 60% free, more preferably at least 75% free, and more preferably at least 90% free from other components with which they are associated. The terms "purify" and "purifying" denote carrying out one or more steps to generate a purified molecule.

The term "resolving" or "resolution" when used herein in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" as used herein refers to a reaction product wherein one enantiomer is produced in excess of the other, and is defined for a mixture of (+)- and (−)-enantiomers, with the composition given as the mole or weight or volume fraction F(+) and F(−) (where the sum of F(+) and F(−)=1). The enantiomeric excess is defined as (F(+)−F(−)). The percent enantiomeric excess is defined by 100×(F(+)−F(−)). The "purity" of an enantiomer is described by it's ee or percent ee value.

Whether expressed as a "purified enantiomer" or a "pure enantiomeric" or a "resolved enantiomer," or "a compound in enantiomeric excess", the terms as used herein are meant to indicate that the amount of one enantiomer exceeds the amount of the other. Thus, when referring to an enantiomer preparation, both (or either) of the percent of the major enantiomer (e.g., by mole or by weight or by volume) and (or) the percent enantiomeric excess of the major enantiomer may be used to determine whether the preparation represents a purified enantiomer preparation.

The term "enantiomeric purity" or "enantiomer purity" of an isomer as used herein refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" as used herein are meant to indicate a preparation (e.g., derived from non optically active starting material, substrate, or intermediate) wherein one enantiomer has been enriched over the other, and more preferably, wherein the other enantiomer represents less than 20%, more preferably less than 10%, yet more preferably less than 5%, and still more preferably, less than 2% of the enantiomer or enantiomer preparation.

The terms "purified enantiomer," "resolved enantiomer" and "purified enantiomer preparation" as used herein are meant to indicate a preparation (e.g., derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10%, yet more preferably less than 5%, and still more preferably less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," as used herein refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it generally is desirable for one of the enantiomers to be obtained in large excess. This is achieved by terminating the conversion at a certain degree of conversion.

The term "hydrido" as used herein denotes a single hydrogen atom (H). This hydrido group may be attached, for example, to an oxygen atom to form a hydroxyl group; or, as another example, two hydrido groups may be attached to a carbon atom to form a —CH$_2$— group.

The term "alkyl" as used herein, whether used alone or within other terms such as "hydroxyalkyl," embraces linear or branched radicals having from 1 to 20, more preferably from 1 to 10, yet more preferably from 1 to 4 carbon atoms, and most preferably has one carbon atom. For some substituents, more preferred alkyl radicals are "lower alkyl," that is an alkyl having 1 to 10 carbon atoms, yet more preferably from 1 to 4 carbon atoms, and most preferably one carbon atom. An alkyl as used herein includes hydrocarbyl, halocarbyl, and hydrohalocarbyl moieties.

The term "cycloalkyl" as used herein embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms, any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, more preferably one to four carbon atoms, such as methoxy and ethoxy group. The term "alkoxyalkyl" also embraces alkyl radicals having two or more alkoxy groups attached to the alkyl radical, that is, to form monoalkoxyalkyl and dialkoxyalkyl groups. The term "alkylthio" embraces radicals containing a linear or branched alkyl group, of one to about ten carbon atoms attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl, n-hexyl, n-heptyl, n-octyl, n-nonyl, n-decyl, n-undecyl, n-dodecyl, n-tridecyl, n-tetradecyl and n-hexadecyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

The terms "pharmaceutically acceptable," "physiologically tolerable" and grammatical variations thereof, as used herein to refer to compositions, carriers, diluents and reagents, are used interchangeably and represent that the materials are capable of administration to or upon a subject and that the materials do not substantially produce an undesirable effect such as, for example, adverse or allergic reactions, dizziness, gastric upset, toxicity and the like, when administered to a subject. Preferably also, the pharmaceutically acceptable material does not substantially reduce the effectiveness of any of the invention's Formulae A-F in reducing one or more symptoms of disease.

The terms "pharmaceutically effective amount," "therapeutically effective amount," "biologically effective amount," and "therapeutic amount" are used interchangeably herein to refer to an amount which is sufficient to achieve a desired result, whether quantitative or qualitative. In particular, a pharmaceutically effective amount is that amount that results in the reduction, delay, or elimination of undesirable effects (such as pathological, clinical, biochemical and the like) in the subject.

The term "therapeutically effective time" refers to the period of time during which a pharmaceutically effective amount of a compound is administered, and that is sufficient reduce one or more symptoms of a disease or condition.

The term "concomitant" when in reference to the relationship between administration of a compound and a disease symptoms means that administration occurs at the same time as, or during, manifestation of the disease symptom.

DESCRIPTION OF THE INVENTION

The invention provides compositions and methods for reducing one or more symptoms of an autoimmune disease, inflammatory disease, and/or transplant rejection, by the administration to a subject in need thereof a pharmaceutically effective amount of a purified compound of any one of Formulae A-E. The invention's methods are useful for the prevention, amelioration, and treatment of autoimmune disease, inflammatory disease, and/or transplant rejection.

The invention was premised, in part, on the inventor's discovery that piceatannol when administered to healthy animals was very well tolerated by the animals, i.e. the inventor did not detect any acute or chronic toxicity even after repeated high dose (1 mg) intraperitoneal injections of piceatannol. While investigating lipopolysaccharide (LPS) activation of interferon regulated genes, the inventor also discovered that the natural stilbene compounds piceatannol and resveratrol block LPS induced gene expression (e.g., RANTES, MCP-1, TNF) in the micromolar range of concentration. Based on these results, the inventor further investigated the effect of the exemplary compound piceatannol on septic shock in an animal model.

Surprisingly, the inventor discovered that a single administration of piceatannol in an animal model of sepsis is capable of providing up to 100% protection against endotoxic shock (Example 1). In addition, piceatannol administration several hours after LPS challenge in an animal model of sepsis rescued approximately 50% of the animals. Without limiting the invention to any particular mechanism, it is the inventor's contemplation that piceatannol's effectiveness in reducing disease symptoms that are associated with inflammatory disease and transplant rejection may be mediated by piceatannol's interference with LPS mediated signal transduction in vivo. Indeed, the inventor has demonstrated that piceatannol blocks LPS induced gene expression (e.g., RANTES, MCP-1, ISG54) in the micromolar range in vitro, and that production of TNFα and IL-6 in response to LPS is also inhibited by piceatannol in vitro.

Surprisingly also, the inventor discovered that administering the exemplary piceatannol in an animal model of multiple sclerosis completely halted disease progression (Example 3).

The invention is further described below under (A) Compounds Of The Invention, and (B) Reducing Symptoms Of Disease.

A. Compounds of the Invention

The invention contemplates compounds of Formula A, B, C, D and/or E as further discussed below. One advantage of the invention's compounds is their low toxicity. For example, data herein demonstrates the low toxicity of piceatannol in vivo (Examples 1 and 3). Another advantage of the invention's compounds is their ready availability. Indeed, many of the invention's compounds are found in plants such as chinese rhubarb, *euphorbia* sp., grapes, peanut, and sugar cane. The invention's compounds are also useful because of their efficient absorption by the body. For example, greater than 20% of intestinally ingested resveratrol is absorbed into the blood stream.

In one embodiment, the invention's methods employ compounds of Formula B:

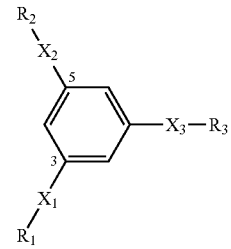

In one embodiment of Formula B, (a) $X_3$ is from 1 to 10 atoms independently selected from one or more of oxygen, carbon, sulfur, nitrogen, and phosphorus, and wherein the atoms are linked to each other by one or more single bonds or one or more double bonds, and wherein each of the atoms is optionally further linked to a hydrido or hydroxyl, (b) $R_3$ is selected from $(-H)_x$ wherein x is selected from 1, 2 and 3, straight or branched chain alkyl having from 1 to 20 carbon atoms, cyclopentyl, cyclohexyl, benzyl, pyrane, furane, pyridine, pyrimidine, and a moiety having the following structure of Formula C,

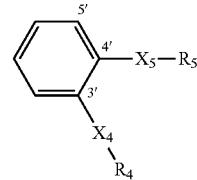

(c) each of $X_1$, $X_2$, $X_4$, and $X_5$ is independently selected from hydrogen, hydroxyl, and an alkoxyl having from 1 to 10 carbon atoms, (d) each of $R_1$, $R_2$, $R_4$ and $R_5$ is independently selected from hydrogen, alkyl having from 1 to 20 carbon atoms, pyranose sugar, and furanose sugar, and (e) the carbon atom at position 4 of Formula B, position 5' of Formula C, or position 4 of Formula B and position 5' of Formula C is covalently linked to a hydrido, hydroxy, alkoxyl having from 1 to 4 carbon atoms, pyranose sugar, or furanose sugar, thereby reducing one or more symptoms of the condition. In one preferred embodiment, each of $R_1$, $R_2$, $R_4$, and $R_5$ is selected from —H, —CH$_3$, and —C$_2$H$_5$. Alternatively, $X_3$ is selected from —C=C— and —CH—CH—. In another alternative, $R_1$, $R_2$, $R_4$, and $R_5$ is an alkyl having from 1 to 4 carbon atoms. In a further alternative, $R_1$, $R_2$, $R_4$, and $R_5$ is an alkyl having one carbon atom.

In another alternative, $R_3$ of Formula B has a structure of Formula B, i.e., two structures of Formula B are linked to each other via $X_3$.

In yet another embodiment of Formula B, $X_3$ is selected from $O_n$, $(CY)_w$, $(CY_2)_w$, $(SY)_w$, $(SY_2)_w$, $(NY)_w$, $(NY_2)_w$, $(PY)_w$, and $(PY_2)_w$. In another embodiment, $R_3$ is selected from $(-H)_x$, straight or branched chain alkyl having from 1 to 20 carbon atoms, cyclopentyl, cyclohexyl, benzyl, purane, furane, pyridine, pyrimidine, and Formula C:

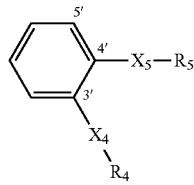

In a preferred embodiment, x is selected from 1, 2 and 3. In one embodiment, each of $X_1$, $X_2$, $X_4$, and $X_5$ is independently selected from H, O, $CY_2$, $SY_2$, $NY_2$, and $PY_2$. In a further embodiment, Y is independently selected from —H and —OH. In another embodiment, w is an integer from 1 to 20, more preferably from 1 to 10, yet more preferably from 1 to 4, even more preferably from 1 to 2, and most preferably is 2. In a further embodiment, n is an integer from 1 to 20, more preferably from 1 to 10, and most preferably is selected from 0, 1, 2, 3, and 4. In one embodiment, each of $R_1$, $R_2$, $R_4$ and $R_5$ is independently selected from $(-H)_x$ and an alkyl having from 1 to 20 carbon atoms.

In one embodiment, each of $X_1$ and $X_2$ is O. In another embodiment, each of $R_1$, $R_2$, $R_4$, and $R_5$ is selected from —H, —CH$_3$, and —C$_2$H$_5$. In another preferred embodiment, $X_3$ is selected from —C=C— and —CH—CH—, more preferably is —C=C—. In a particularly preferred embodiment, Y is —H. In one preferred embodiment, the alkyl has from 1 to 20, more preferably from 1 to 10, yet more preferably from 1 to 4 carbon atoms, and most preferably has one carbon atom.

In another embodiment, the alkyl is selected from hydrocarbyl, halocarbyl, and hydrohalocarbyl, and the halogen in the halocarbyl or hydrohalocarbyl is chlorine, bromine, or fluorine. In a further embodiment, the pyrane is selected from glucopyrane, mannopyrane, galactopyrane, and fructopyrane. In yet another embodiment, the fume is selected from arabinofurane and ribofurane.

In one embodiment of Formula B, the carbon atom at position 4 of Formula B, position 5' of Formula C, or position 4 of Formula B and position 5' of Formula C is covalently linked to a hydrido, hydroxy, alkoxyl having from 1 to 4 carbon atoms, pyranose sugar, or furanose sugar.

In an alternative embodiment, the compounds of the invention are of Formula D:

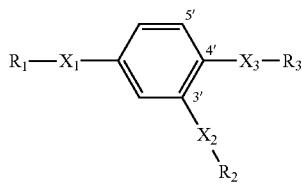

In one embodiment of Formula D, wherein: (a) $X_1$ is from 1 to 10 atoms independently selected from one or more of oxygen, carbon, sulfur, nitrogen, and phosphorus, and wherein the atoms are linked to each other by one or more single bonds or one or more double bonds, and wherein each of the oxygen, carbon, sulfur, nitrogen, and phosphorus atoms is optionally further linked to a hydrido or hydroxyl, (b) $R_1$ is selected from $(-H)_x$ wherein x is selected from 1, 2 and 3, straight or branched chain alkyl having from 1 to 20 carbon atoms, cyclopentyl, cyclohexyl, benzyl, pyrane, furane, pyridine, pyrimidine, and a moiety having the following structure of Formula E

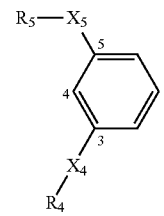

(d) each of $X_2$, $X_3$, $X_4$, and $X_5$ is independently selected from hydrogen, oxygen, alkyl having from 1 to 4 carbon atoms, alkoxyl having from 1 to 4 carbon atoms, $SY_2$, $NY_2$, and $PY_2$ wherein Y is independently selected from —H and —OH, (h) each of $R_2$, $R_3$, $R_4$ and $R_5$ is independently selected from $(-H)_x$ wherein x is selected from 1, 2 and 3, an alkyl having from 1 to 20 carbon atoms, pyranose sugar, and furanose sugar, and (i) the carbon atom at position 5' of Formula D, position 4 of Formula E, or position 5' of Formula D and position 4 of Formula E is covalently linked to a hydrido, hydroxy, alkoxyl having from 1 to 4 carbon atoms, pyranose sugar, or furanose sugar, thereby reducing one or more symptoms of the condition.

In another embodiment, $R_1$ of Formula D has a structure of Formula D, i.e., two structures of Formula D are linked to each other via $X_1$.

In another embodiment of Formula D, $X_1$ is selected from $O_1$, $(CY)_w$, $(CY_2)_w$, $(SY)_w$, $(SY_2)_w$, $(NY)_w$, $(NY_2)_w$, $(PY)_w$, and $(PY_2)_w$. In another embodiment, $R_1$ is selected from $(-H)_x$, straight or branched chain alkyl having from 1 to 20 carbon atoms, cyclopentyl, cyclohexyl, benzyl, purane, furane, pyridine, pyrimidine, and Formula E:

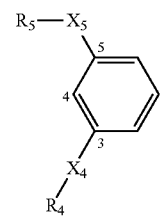

In a preferred embodiment, x is selected from 1, 2 and 3; each of $X_2$, $X_3$, $X_4$, and $X_5$ is independently selected from H, O, $CY_2$, $SY_2$, $NY_2$, and $PY_2$; Y is independently selected from —H and —OH; w is an integer from 1 to 20, more preferably from 1 to 10, yet more preferably from 10, even more preferably from 1 to 4 and most preferably is 2; n is an integer from 1 to 20, more preferably from 1 to 10, and most preferably is selected from 0, 1, 2, 3, and 4; and each of $R_2$, $R_3$, $R_4$ and $R_5$ is independently selected from $(-H)_x$ and an alkyl having from 1 to 20 carbon atoms.

In one preferred embodiment, each of $X_4$ and $X_5$ is O. In another embodiment, each of $R_2$, $R_3$, $R_4$, and $R_5$ is selected from —H, —CH$_3$, and —C$_2$H$_5$. In a further embodiment, $X_1$ is selected from —C=C— and —CH—CH—. In another embodiment, Y is —H. In a further embodiment, the alkyl has from 1 to 4 carbon atoms, more preferably has one carbon atom. In another embodiment, the alkyl is selected from hydrocarbyl, halocarbyl, and hydrohalocarbyl, wherein the halogen in the halocarbyl or hydrohalocarbyl is chlorine, bromine, or fluorine. In yet another embodiment, the pyrane is selected from glucopyrane, mannopyrane, galactopyrane, and fructopyrane. Preferably, the furane is selected from arabinofurane and ribofurane.

In a particularly preferred embodiment, the purified compound has Formula A:

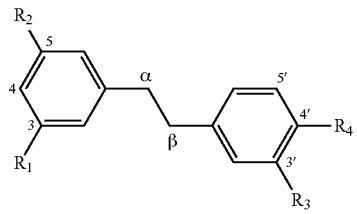

In one embodiment of Formula A, (a) each of $R_1$, $R_2$, $R_3$ and $R_4$ is independently selected from hydrido, hydroxy, alkoxyl having from 1 to 4 carbon atoms, pyranose sugar, and furanose sugar, (b) each of α and β is from 1 to 5 atoms independently selected from one or more of oxygen, carbon, sulfur, nitrogen, and phosphorus, wherein the oxygen, carbon, sulfur, nitrogen, and phosphorus atoms are linked to each other by one or more single bonds or one or more double bonds, and wherein each of the oxygen, carbon, sulfur, nitrogen, and phosphorus atoms is optionally further linked to a hydrido or hydroxyl, and (c) the carbon atom at position 4, position 5', or positions 4 and 5' is covalently linked to a hydrido, hydroxy, alkoxyl having from 1 to 4 carbon atoms, pyranose sugar, or furanose sugar, thereby reducing one or more symptoms of the condition. In one preferred embodiment, each of α and β is —CH—, preferably, each of $R_1$ and $R_2$ is —OH, and alternatively, each of $R_1$ and $R_2$ is independently selected from —OCH$_3$ and —OCH$_2$—CH$_3$, while more preferably, each of $R_1$ and $R_2$ is —OCH$_3$. Alternatively, each of $R_1$, $R_2$, $R_3$, and $R_4$ is —OH, and the compound is piceatannol. In another alternative, one or more of $R_1$, $R_2$, $R_3$, and $R_4$ is —OCH$_3$, preferably, wherein each of $R_1$, $R_2$, $R_3$, and $R_4$ is —OCH$_3$, and the compound is tetramethoxy-stilbene. In a further alternative, one or more of $R_1$, $R_2$, $R_3$, and $R_4$ is —OCH$_2$—CH$_3$, more preferably, each of $R_1$, $R_2$, $R_3$, and $R_4$ is —OCH$_2$—CH$_3$, and the compound is tetraethoxy-stilbene. Alternatively, each of $R_1$, $R_2$, and $R_4$ is —OH, $R_3$ is —H, and the compound is resveratrol. In a further alternative, one or more of $R_1$, $R_2$, and $R_4$ is —OCH$_3$, and $R_3$ is —H, more preferably, each of $R_1$, $R_2$, and $R_4$ is —OCH$_3$, $R_3$ is —H, and the compound is trimethoxy-stilbene. In another alternative, one or more of $R_1$, $R_2$, and $R_4$ is —OCH$_2$—CH$_3$, and $R_3$ is —H, more preferably each of $R_1$, $R_2$, and $R_4$ is —OCH$_2$—CH$_3$, and $R_3$ is —H. In yet another alternative, each of $R_1$, $R_2$, and $R_3$ is —OH, $R_4$ is —OCH$_3$, and the compound is rhapontigenin. In another embodiment, the compound is piceatannol, tetramethoxy-piceatannol, resveratrol, or rhapontigenin.

In another embodiment for Formula A, (a) each of $R_1$ and $R_2$ is independently selected from —OH and —O(CH$_2$)$_n$—CH$_3$, (b) each of $R_3$ and $R_4$ is independently selected from —H, —OH, and —O(CH$_2$)$_n$—CH$_3$, (c) each of α and β is independently selected from O$_n$, (CY)$_w$, (Cy$_2$)$_w$, (SY)$_w$, (SY$_2$)$_w$, (NY)$_w$, (NY$_2$)$_w$, (PY)$_w$, and (PY$_2$)$_w$, (d) n is selected from 0, 1, 2, 3, and 4, (e) w is selected from 1, 2, 3, and 4, and (f) and (c) the carbon atom at position 4, position 5', or positions 4 and 5' is covalently linked to a hydrido, hydroxy, alkoxyl having from 1 to 4 carbon atoms, pyranose sugar, or furanose sugar.

Another alternative for Formula A is where (a) each of $R_1$ and $R_2$ is independently selected from —H, —OH and —O(CH$_2$)$_n$—CH$_3$, (b) each of $R_3$ and $R_4$ is independently selected from —OH and —O(CH$_2$)$_n$—CH$_3$, (c) each of α and β is independently selected from O$_n$, (CY)$_w$, (CY$_2$)$_w$, (SY)$_w$, (SY$_2$)$_w$, (NY)$_w$, (NY$_2$)$_w$, (PY)$_w$, and (PY$_2$)$_w$, (d) n is selected from 0, 1, 2, 3, and 4, (e) w is selected from 1, 2, 3, and 4, and (f) the carbon atom at position 4, position 5', or positions 4 and 5' is covalently linked to a hydrido, hydroxy, alkoxyl having from 1 to 4 carbon atoms, pyranose sugar, or furanose sugar.

For Formula A, it is preferred that each of α and β is —CH—, more preferably, each of $R_1$ and $R_2$ is —OH. Alternatively, each of $R_1$ and $R_2$ is independently selected from —OCH$_3$ and —OCH$_2$—CH$_3$, more preferably, each of $R_1$ and $R_2$ is —OCH$_3$. In an alternative embodiment, each of $R_1$, $R_2$, $R_3$, and $R_4$ is —OH, and the compound is piceatannol (FIG. 1). Piceatannol is a naturally derived, partially water soluble stilbene derivative (tetrahydroxy-stilbene, Molecular weight approximately 244.2) that has found limited application in the laboratory as an inhibitor of the tyrosine kinases Syk and ZAP70 (Geahlen, et al. (1989) BBRC 165, no. 1:241-5). Piceatannol acts as a potent inhibitor of the tyrosine kinase Tyk2 (Su, et al. (2000) J Biol Chem 275, no. 17:12661-6).

Figure 2:
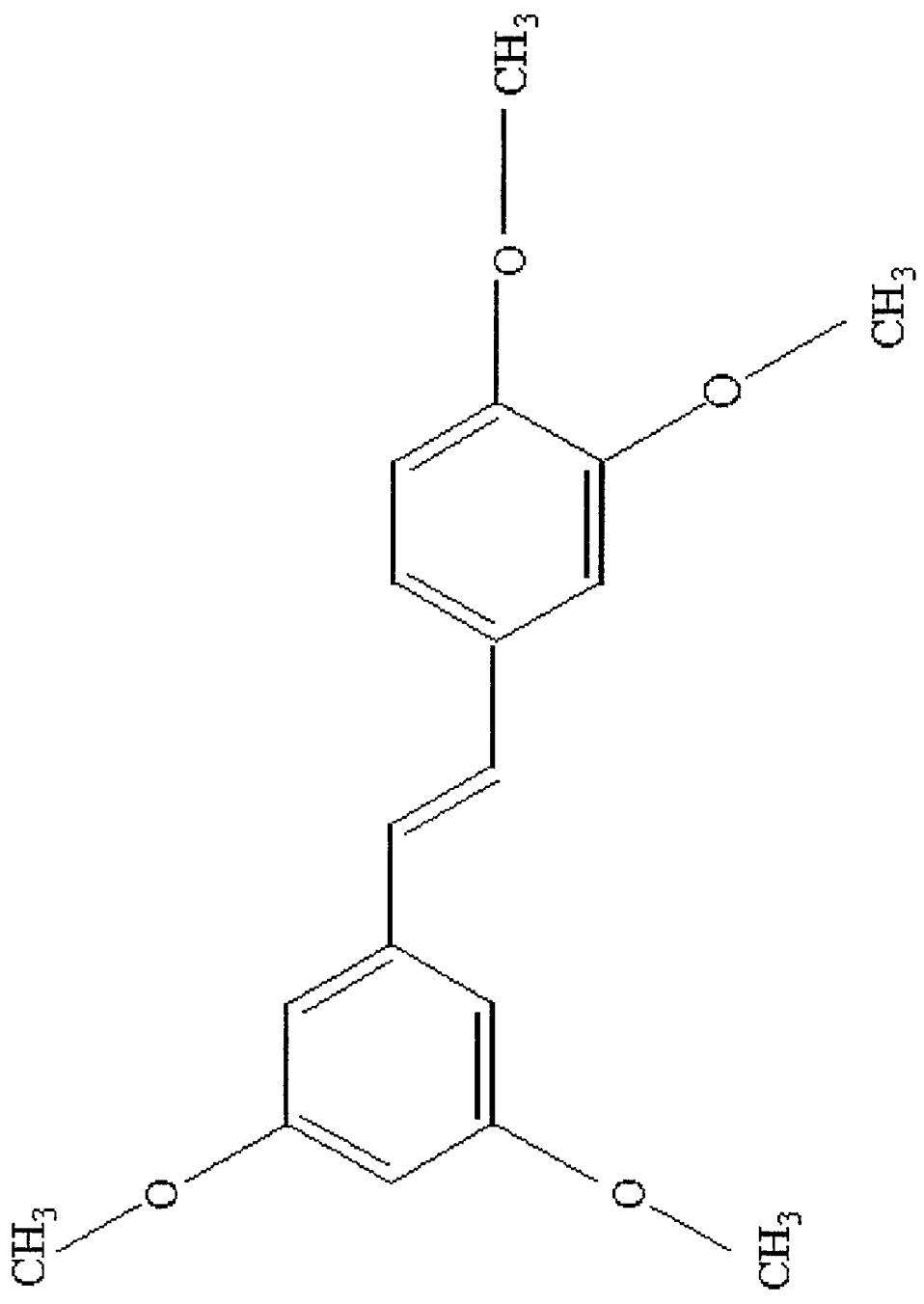
FIG. 2 shows tetramethoxy-stilbene.
Figure 3:
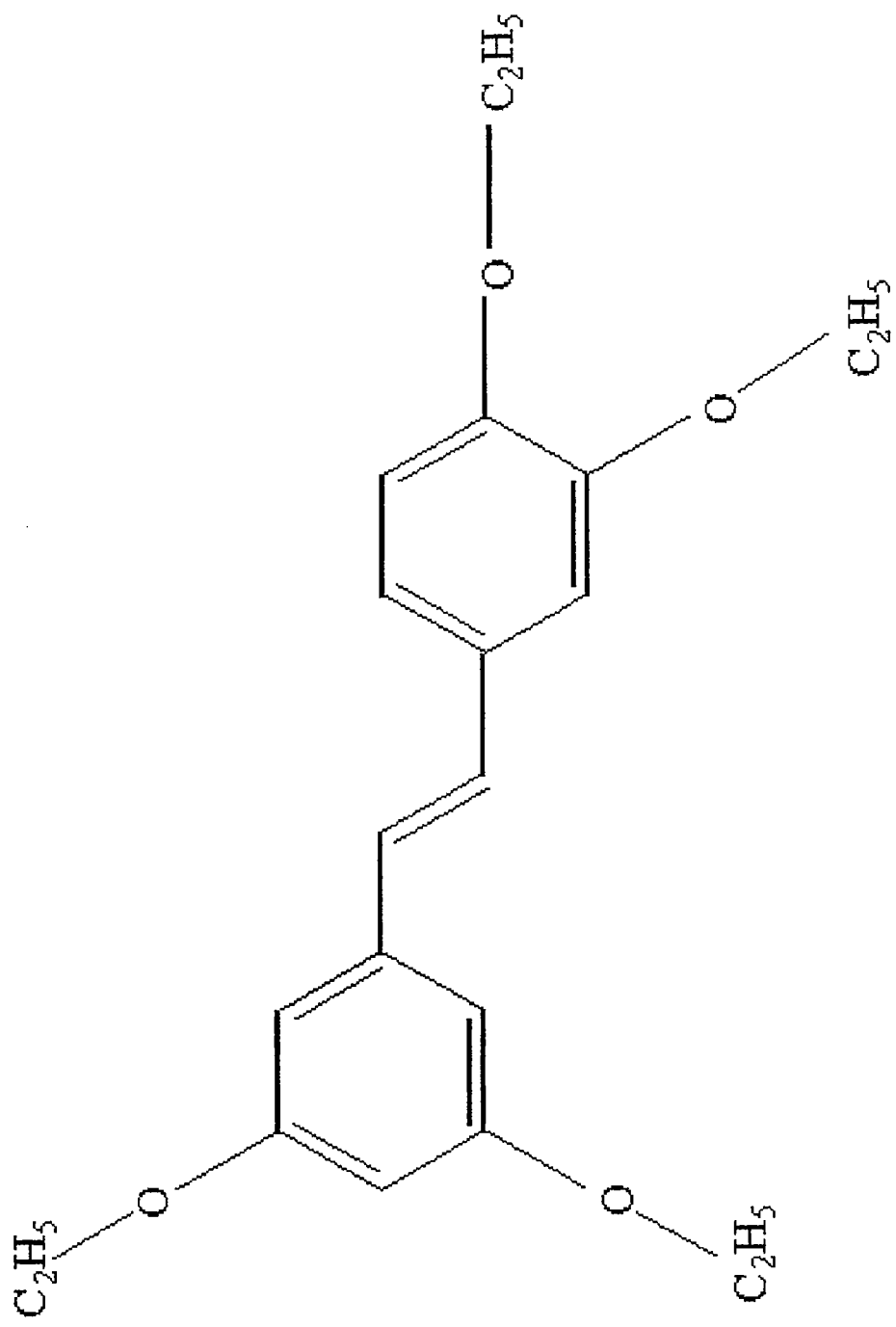
FIG. 3 shows tetraethoxy-stilbene.
Figure 4:
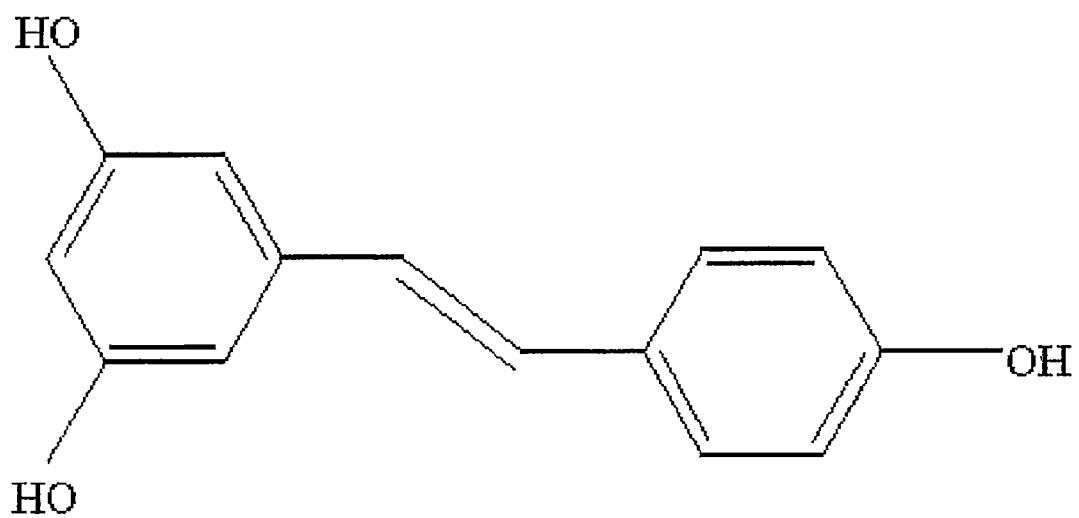
FIG. 4 shows resveratrol.
Figure 5:
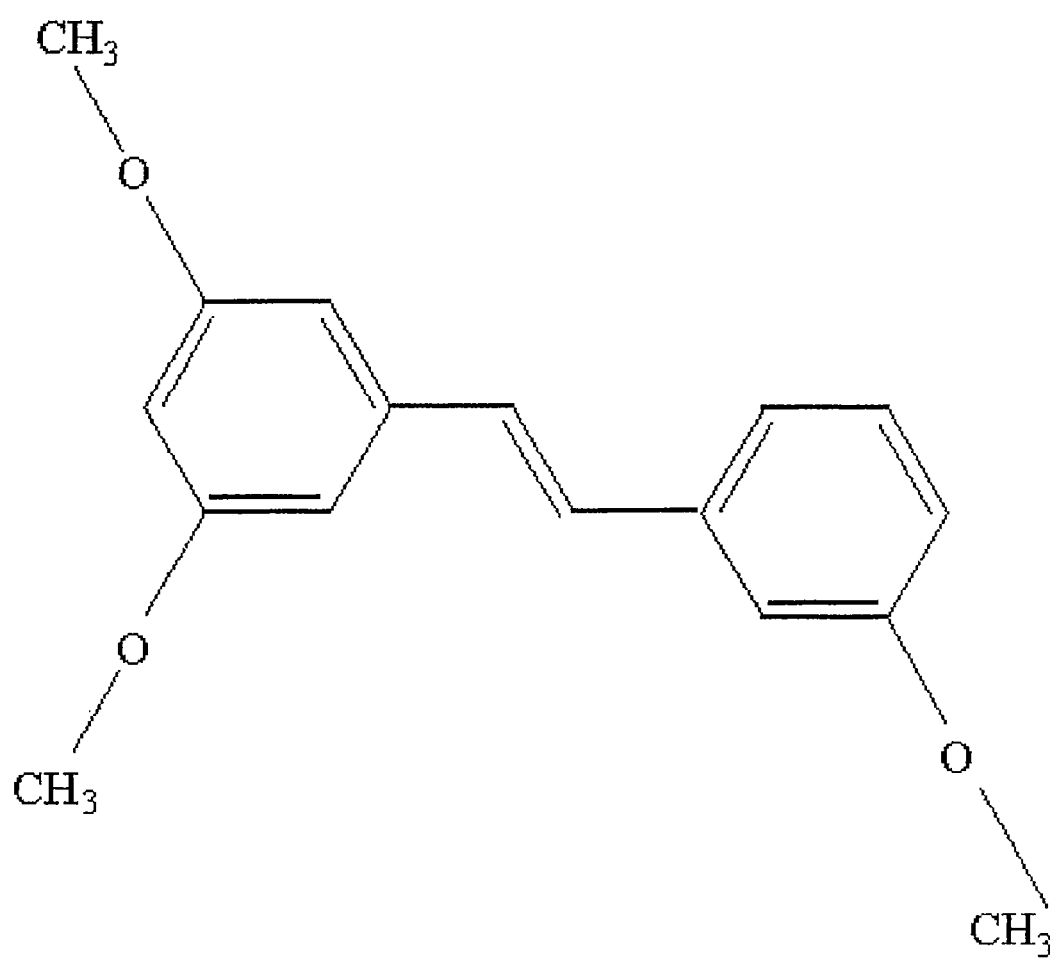
FIG. 5 shows trimethoxy-stilbene.
Figure 6:
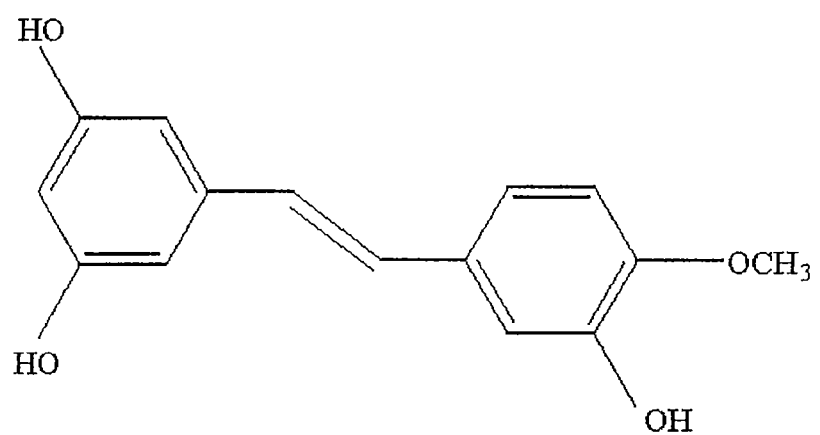
FIG. 6 shows rhapontigenin.

Alternatively, one or more of $R_1$, $R_2$, $R_3$, and $R_4$ is —OCH$_3$, more preferably, each of $R_1$, $R_2$, $R_3$, and $R_4$ is —OCH$_3$, and the compound is tetramethoxy-stilbene (FIG. 2). Yet in another alternative, one or more of $R_1$, $R_2$, $R_3$, and $R_4$ is —OCH$_2$—CH$_3$, more preferably, each of $R_1$, $R_2$, $R_3$, and $R_4$ is —OCH$_2$—CH$_3$, and the compound is tetraethoxy-stilbene (FIG. 3). In a further alternative embodiment, each of $R_1$, $R_2$, and $R_4$ is —OH, $R_3$ is —H, and the compound is resveratrol (FIG. 4). One alternative is that one or more of $R_1$, $R_2$, and $R_4$ is —OCH$_3$, and $R_3$ is —H, preferably where each of $R_1$, $R_2$, and $R_4$ is —OCH$_3$, $R_3$ is —H, and the compound is trimethoxy-stilbene (FIG. 5). In yet another alternative, one or more of $R_1$, $R_2$, and $R_4$ is —OCH$_2$—CH$_3$, and $R_3$ is —H, more preferably, wherein each of $R_1$, $R_2$, and $R_4$ is —OCH$_2$—CH$_3$, and $R_3$ is —H. In another alternative, each of $R_1$, $R_2$, and $R_3$ is —OH, $R_4$ is —OCH$_3$, and the compound is rhapontigenin (FIG. 6).

Figure 7:
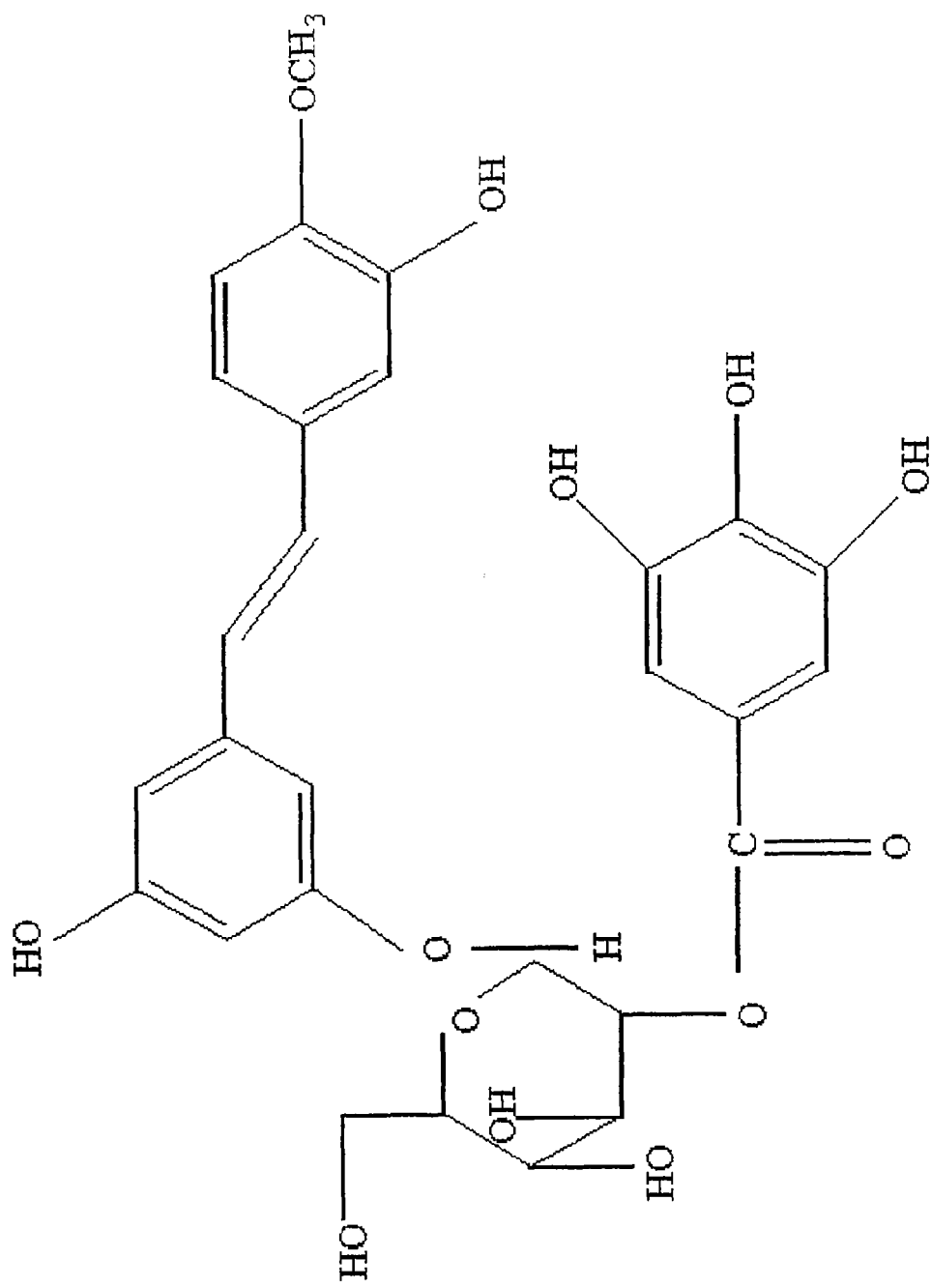
FIG. 7 shows rhaponticin 2"-O-gallate.
Figure 8:
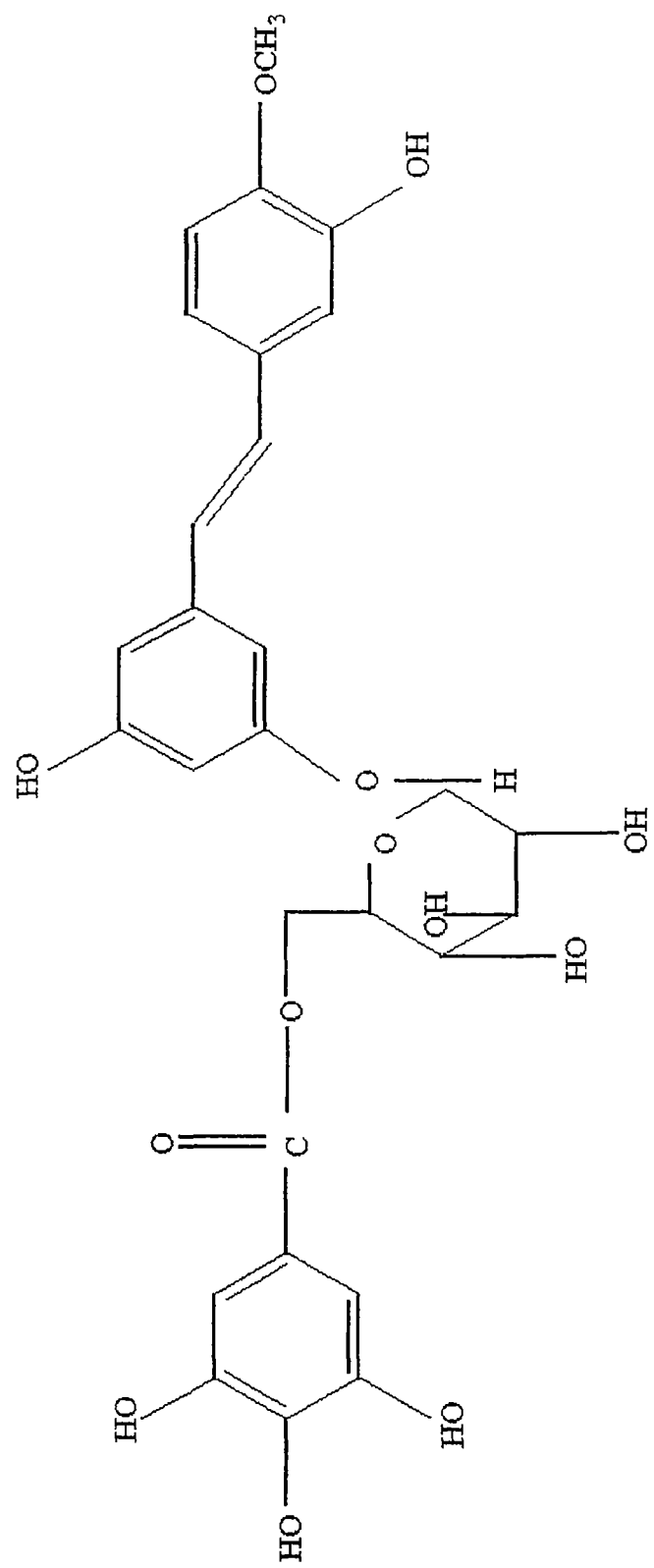
FIG. 8 shows rhaponticin 6"-O-gallate.
Figure 9:
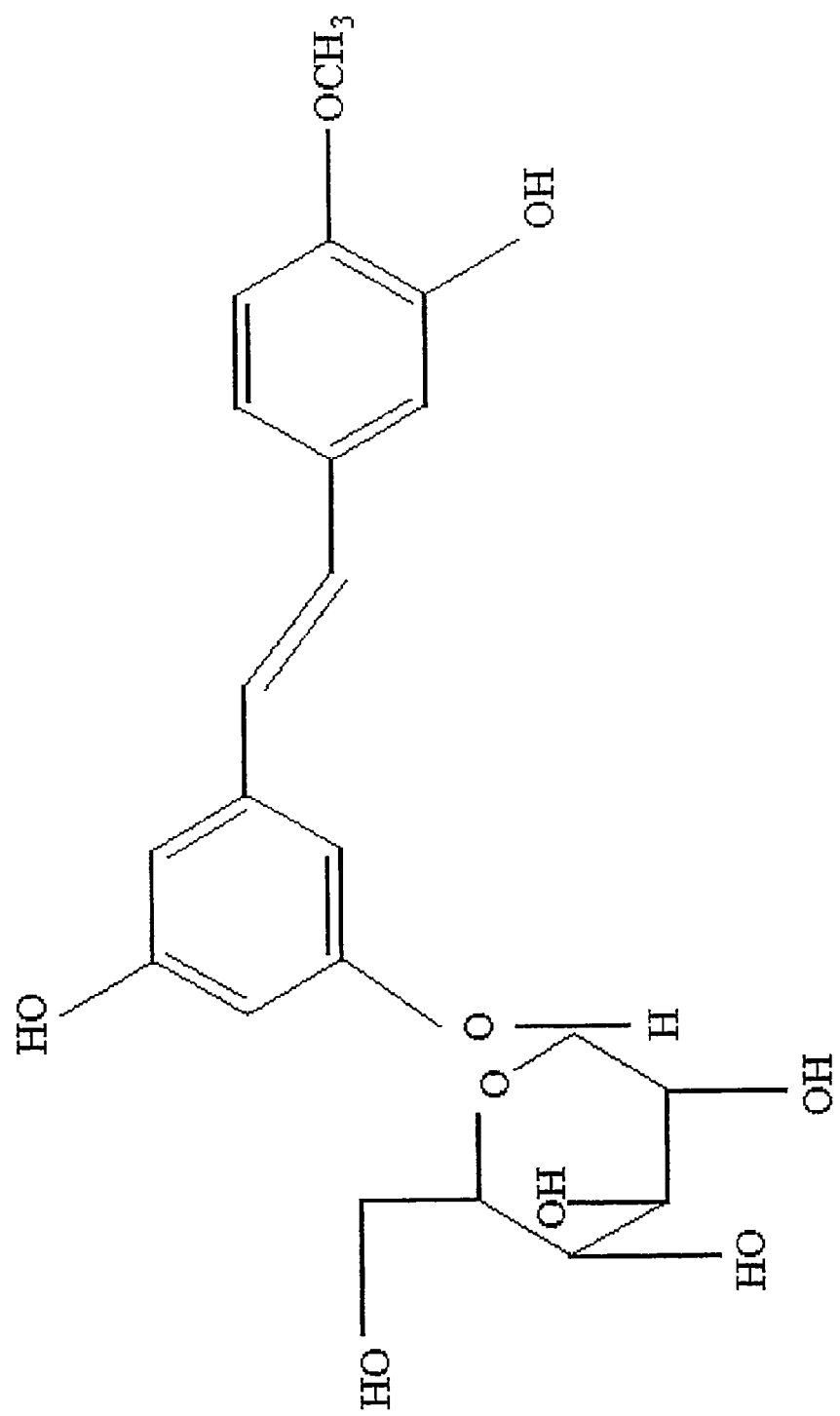
FIG. 9 shows rhaponticin.

In a preferred embodiment, the invention's compounds are glycosylated. Glycosylated compounds of each of Formula A-E are preferred since it is the inventor's view that glycosylation increases solubility and/or efficacy of the compound. Glycosylated compounds of the invention are exemplified by rhaponticin (FIG. 9). For example, with respect to Formula A, it is preferred that $R_1$ is glycosylated to a pyranose sugar or a furanose sugar. Preferably, the pyranose sugar is selected from glucopyranose, mannopyranose, galactopyranose, and fructopyranose. Alternatively, the furanose sugar is selected from arabinofuranose and ribofuranose. In yet another alternative, the sugar is esterified to a galloyl moiety. More preferably, the ester is a 2"-O-gallate ester as exemplified by rhaponticin 2"-O-gallate (FIG. 7). In a preferred embodiment, the ester is a 6"-O-gallate ester as exemplified by rhaponticin 6"-β-gallate (FIG. 8).

In addition to glycosylated derivatives of the invention's compounds, the invention contemplates compounds in either the cis form or trans form as well as polymers of each of the invention's Formulae A-E.

The invention also expressly contemplates pharmaceutically acceptable salts of each of the invention's Formulae A-E. The term "pharmaceutically acceptable salt" embraces any salt that is commonly used to form alkali metal salts and to form addition salts of free acids or free bases, including quaternary ammonium salts. The nature of the salt is not critical, provided that it is pharmaceutically acceptable. Suitable pharmaceutically acceptable acid addition salts of each of the invention's Formulae A-E may be prepared from an inorganic acid or from an organic acid. Examples of such inorganic acids are hydrochloric, hydrobromic, hydroiodic, nitric, carbonic, sulfuric, citric, and phosphoric acid. Appropriate organic acids may be selected from aliphatic, cycloaliphatic, aromatic, araliphatic, heterocyclic, carboxylic and sulfonic classes of organic acids, the latter of which is exemplified by formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Particularly preferred are pharmaceutically acceptable salts such as, without limitation, hydrochlorides, sulfates, citrates, tartrates and phosphates. Suitable pharmaceutically acceptable base addition salts of compounds of each of the invention's Formulae A-E include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of each of the invention's Formulae A-E by reacting, for example, the appropriate acid or base with the compound of each of the invention's Formulae A-E.

Also expressly included within the scope of the invention are isomers of each of the invention's Formulae A-E. The terms "isomer" refers to compounds having the same molecular formula but differing in structure, such as diastereoisomers, regioisomers, conformational isomers, geometric isomers, enantiomers, and the pharmaceutically acceptable salts thereof. Isomers which differ only in configuration and/or conformation are referred to as "stereoisomers." Thus, a "conformational isomer" refers to a compound that exists in different conformational forms. For example, different conformers of a single compound may result from torsional asymmetry due to restricted rotation about an asymmetric single bond, for example because of steric hindrance or ring strain.

Compounds of each of the invention's Formulae A-E can possess one or more asymmetric carbon atoms and are thus capable of existing in the form of optical isomers as well as in the form of racemic or nonracemic mixtures thereof. Optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting a compound of each of the invention's Formulae A-E with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compound of each of the invention's Formulae A-E can likewise be obtained by utilizing optically active starting materials. These isomers may be in the form of a free acid, a free base, an ester or a salt.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Generally, an enantiomer refers to a compound that contains one or more chiral centers, and exists in different optically active forms. When compounds of each of the Formulae A-E contain one chiral center, the compounds exist in two enantiomeric forms and the present invention includes both enantiomers and mixtures of enantiomers. Enantiomers have identical physical properties, such as melting points and boiling points, and also have identical spectroscopic properties. Enantiomers differ from each other with respect to their interaction with plane-polarized light and with respect to biological activity.

For enantiomers, the designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" for enantiomers are employed to designate the sign of rotation of plane-polarized light by the compound, with (−) meaning that the compound is levorotatory (rotates to the left). A compound prefixed with (+) is dextrorotatory (rotates to the right).

Enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The invention further contemplates diasteriomeric forms of each of the inventions Formulae A-E. The term "diastereoisomeric" when in reference to the form of a compound of any one of Formulae A-E refers to a compound that contains more than one chiral center. The diastereoisomeric pairs may be separated by methods known to those skilled in the art, for example chromatography or crystallization, and the individual enantiomers within each pair may be separated as described above. The present invention includes each diastereoisomer of compounds of each of Formula A-E and mixtures thereof.

Furthermore, the invention also expressly contemplates solvates (such as hydrates), tautomers, and zwitterionic forms of each of Formulae A-E and their salts.

In one preferred embodiment, the compounds of the invention include piceatannol (FIG. 1) (also referred to herein as 3,3',4,5'-tetrahydroxy-trans-stilbene or tetrahydroxy-stilbene) and resveratrol (FIG. 4) (trihydroxy-stilbene). Resveratrol and piceatannol are naturally derived, water soluble stilbene derivatives that are found in many plants with a long-standing history of human consumption (e.g., grapes, *euphorbia* sp., rhubarb, etc.) (Kageura, et al. (2001) Bioorg Med Chem 9, no. 7:1887-93; Ko, et al. (1999) Arch Pharm Res 22, no. 4:401-3; Bavaresco, et al. (1999) Drugs Exp Clin Res 25, no. 2-3:57-63; Waffo Teguo, et al. (1998) J Nat Prod 61, no. 5:655-7). Resveratrol is the active ingredient in red wine that accounts for the low incidence of heart disease in the French population despite a diet rich in fat ("French Paradox") (Palmieri, et al. (1999) Drugs Exp Clin Res 25, no. 2-3:79-85).

In yet another preferred embodiment the hydroxyl group on the cyclopentyl, cyclohexyl, benzyl, purane, furane, pyridine, and/or pyrimidine moiety are replaced by alkyl groups. Exemplary compounds include, without limitation, tetramethoxy-stilbene (FIG. 2), tetra-ethoxystilbene (FIG. 3), and tri-methoxy-stilbene (FIG. 5). It is the inventor's view that since phenolic hydroxyl-compounds are typically rapidly metabolized and inactivated in vivo by conjugation of glucuronic acid to the hydroxyl groups, then modifying the invention's compounds to avoid the availability of free OH-groups would increase the biological half-life of the compounds. Indeed, the inventor has determined that tetramethoxy-piceatannol (TMP) in vitro is as effective as piceatannol in the inhibition of LPS-mediated ISG induction.

Methods for producing compounds of the invention are known in the art such as those for making hydroxylated stilbenes (Moreana-Manas, M. et al, Anal Quim (1985) 81:157-161; Jeandet, P. et al, Am J. Enol Vitic (1991) 42:41-6; Goldberg D M et al. Anal Chem (1994) 66:3959-63, Murakami, S et al, Biochem Pharmacol. (1992) 44:1947-51; and Thakkar, K et al, J. Med Chem (1993) 36:2650-51). Additionally, piceatannol is available commercially from Sigma Chemical Co., St. Louis, Mo., CalBiochem, and A.G. Scientific; resveratrol is commercially available from Sigma; and tetramethoxy-piceatannol (TMP) is synthesized by Biocon India Ltd. (India).

Furthermore, other compounds falling within the scope of the invention may be isolated from plant tissue, such as the rhizome of *R. undulatum* [Kaguera et al. (2001) supra]. In particular, plants that are natural sources for resveratrols include *Vitis vinifera* and *Polygonum cuspidatum* (Huzhang). The concentration of resveratrol in *P. cuspidatum* is much higher than in *V. vinifera*. Several protocols are known in the art for isolating resveratrols from plant materials [Raventos et al., J. Agric. Food Chem., 43, pp. 281-283 (1995); Langcake et al., Physiological Plant Pathology, vol. 9, pp. 77-86 (1976)]. Moreover, resveratrol and its derivatives may be isolated from transgenic plant tissue that expresses exogenous grapevine resveratrol synthase as described in U.S. Pat. No. 5,500,367 issued Mar. 19, 1996 to Hain et al., incorporated by reference in its entirety.

B. Reducing Symptoms of Disease

The invention contemplates using the invention's compounds of any one of Formulae A-E to reduce one or more symptoms of an autoimmune disease, inflammatory disease, and/or transplant rejection.

The term "disease" refers to an interruption, cessation, or disorder of body function, systems, or organs. The term "disease" includes responses to injuries, especially if such responses are excessive, produce symptoms that excessively interfere with normal activities of an individual, and/or the tissue does not heal normally (where excessive is characterized as the degree of interference, or the length of the interference).

The term "condition" is used to refer to a disease and/or a response to injury (e.g., trauma, etc.) or treatment (e.g., surgery, transplantation of tissue from a donor, etc.).

The terms "reducing one or more symptoms of a disease," "reducing the severity of a pathological condition," "diminishing the severity of a pathological condition, and "reducing symptoms associated with a pathological condition" mean that one or more adverse clinical signs or symptoms associated with the pathological condition or disease are reduced, delayed, or eliminated, as compared to the level of the pathological condition or disease in the absence of treatment with the particular composition or method. The effects of diminishing the severity of a pathological condition may be determined by methods routine to those skilled in the art including, but not limited to, angiography, ultrasonic evaluation, fluoroscopic imaging, fiber optic endoscopic examination, biopsy and histology, blood tests, which can be used to determine relevant enzyme levels or circulating antigen or antibody, imaging tests which can be used to detect a decrease in inflammation, or an ophthalmic procedure which can be used to identify a reduction in the number of blood vessels in the retina of a diabetic patient. Such clinical tests are selected based on the particular pathological condition being treated. A reduction in the severity of a pathological condition also can be detected based on comments made by the patient being treated, for example, that a patient suffering from arthritis feels less pain or has greater joint mobility, or that a patient with diabetic retinopathy can see more clearly, or the like.

The term "autoimmune disease" as used herein refers to a disease in which the production of antibodies and/or T cells directed against a self-antigen is a cause of the pathology of the disease. Diseases in which autoantibodies are involved include, for example, bullous pemphigoid, Graves' disease, some forms of diabetes mellitus, myasthenia gravis, systemic lupus erythematosus, pernicious anaemia, autoimmune hemolytic anaemia, glomerulonephritis, autoimmune thrombocytopenic purpura. Self-reactive T cells are thought to be involved in rheumatoid arthritis and insulin-dependent diabetes mellitus.

It is contemplated that the invention's compounds are useful in autoimmune diseases such as, without limitation, Sjogren's disease, type I diabetes, insulin dependent diabetes mellitus, scleroderma, polymyositis, chronic active hepatitis, mixed connective tissue disease, primary biliary cirrhosis, pernicious anemia, autoimmune hemolytic anemia, autoimmune thyroiditis, idiopathic Addison's disease, vitiligo, gluten-sensitive enteropathy, Grave's disease, myasthenia gravis, neutropenia, idiopathic thrombocytopenia purpura, pemphigus vulgaris, autoimmune infertility, Goodpasture's disease, bullous pemphigoid, discoid lupus, systemic lupus erythematosus, dense deposit disease, Hashimoto's disease, fibromyalagia, arthritis selected from rheumatoid arthritis, gouty arthritis, and juvenile rheumatoid arthritis, an autoimmune disease of blood vessels selected from necrotizing angitis, and granulomatous angitis, or an autoimmune disease of kidney selected from nephritis, glomerulonephritis, and systemic lupus erythematosus.

In one preferred embodiment, the autoimmune disease is inflammatory bowel disease (IBD). IBDs comprise an autoimmune component as well as an inflammatory response to chronic LPS exposure. The fact that IBD can be induced in animal models by adoptive transfer of $CD4^+CD45RB^{hi}$ T cells characterizes this disease as an autoimmune disorder (Kawachi, et al. (2000) BBRC 268, no. 2:547-52). Further evidence for a role of $CD4^+$ TH1 cells is derived from the observation that blocking the effects of IL-12, the cytokine necessary for induction and maintenance of TH1 cells, appears to prevent murine colitis (Neurath, et al. (1995) J Exp Med 182, no. 5:1281-90). Lastly, abrogation of the production of cytokines such as $TNF\alpha$ and IL-6 by macrophages and other innate immune cells also suppresses the pathological process in animal models (Atreya, et al. (2000) Nat Med 6, no. 5:583-8; van Dullemen, et al. (1995) Gastroenterology 109, no. 1:129-35).

The inflammatory process of the intestine allows bacterial products which are abundantly present in the fecal matter to enter the blood stream, where they promote further activation of the immune response (Aoki (1978) Acta Med Okayama 32, no. 2:147-58; Grimm, et al. (1995) Clin Exp Immunol 100, no. 2:291-7). Bacterial endotoxins or lipopolysaccharides (LPSs) have been detected in the plasma of IBD patients, and pro-inflammatory cytokines and chemokines have been detected in elevated amounts in mucosal tissue and/or in peripheral blood, thus suggesting a monocyte/macrophage stimulation by enteric bacteria and/or their constituents (e.g., LPS). This in turn exacerbates the inflammatory processes in the intestine and further increases the mucosal damage, which allows even more LPS and similar components to cross the intestinal barrier. This self-feeding process ultimately leads to a steadily accelerated disease progression.

The term "inflammatory" when used in reference to a disease or condition refers to a pathological process caused by, resulting from, or resulting in inflammation that is inappropriate and/or does not resolve in the normal manner but rather persists and results in an inflammatory state. Inflammation results in response to an injury or abnormal stimulation caused by a physical, chemical, or biologic agent; these reactions include the local reactions and resulting morphologic changes, destruction or removal of the injurious material, and responses that lead to repair and healing. Inflammatory disease and conditions may be systemic (e.g., lupus) or localized to particular tissues or organs. One underlying theme in inflammatory disease is a perturbation of the cellular immune response that results in recognition of proteins, such as host proteins (antigens), as foreign. Thus the inflammatory response becomes misdirected at host tissues with effector cells targeting specific organs or tissues often resulting in irreversible damage. The self-recognition aspect of auto-immune disease is often reflected by the clonal expansion of T-cell subsets characterized by a particular T-cell receptor (TCR) subtype in the disease state. Often, inflammatory disease is also characterized by an imbalance in the levels of T-helper (Th) subsets (i.e., Th1 cells versus Th2 cells).

Examples of inflammatory diseases include, without limitation, sepsis, septic shock, endotoxic shock, inflammatory bowel disease such as Crohn's disease and ulcerative colitis, multiple sclerosis, inflammatory diseases involving acute or chronic inflammation of bone and/or cartilage in a joint, anaphylactic reaction, nephritis, asthma, conjunctivitis, inflammatory gum disease, systemic lupus erythematosus, insulin dependent diabetes mellitus, pulmonary sarcoidosis, ocular inflammation, allergy, emphysema, ischemia-reperfusion injury, fibromyalagia, an inflammatory cutaneous disease selected from psoriasis and dermatitis, or an arthritis selected from rheumatoid arthritis, gouty arthritis, juvenile rheumatoid arthritis, and osteoarthritis. In one preferred embodiment, the inflammatory disease is rheumatoid arthritis. Macrophage infiltration and lymphocyte activation are critical steps in the development of rheumatoid arthritis.

The invention is also useful for reducing transplant rejection of tissues (e.g., skin) and organs such as, without limitation, transplants of kidney, liver, heart, bone marrow and pancreas. The term "transplant rejection" refers to any one or more undesirable results, whether clinical or pathological or the like, that are associated with introducing a donor tissue to a recipient animal. Transplant rejection symptoms generally result from histocompatibility variations between donor and recipient that lead to stimulation of the recipient's immune system and/or to an inflammatory response against the donor tissue. From the above, the invention is useful for reducing one or more symptoms of a condition selected from autoimmune disease, inflammatory disease, and transplant rejection.

While an understanding of the mechanism of action of the invention's compounds in any one of the conditions in which it finds utility is not necessary, it is the inventor's view that the compounds disclosed herein block LPS induced gene expression of interferon regulated genes by IRF3. The mechanism by which IFNs activate gene expression has been the target of intense research efforts for many years. The first significant progress was made when the Interferon Stimulated Response Element (ISRE) was identified as an $IFN\alpha/\beta$ inducible enhancer, whose activation is necessary and sufficient for the induction of $IFN\alpha/\beta$ stimulated gene expression (Reich, et al. (1987) Proc. Natl. Acad. Sci. USA 84:6394-6398; Levy, et al. (1986) Proc. Natl. Acad. Sci. USA 83:8929-8933; Lamer, et al. (1984) Proc. Natl. Acad. Sci. USA 81:6733-6737). The Signal Transducer and Activator of Transcription (STAT) 1 and 2 proteins together with Interferon Regulatory Factor 9 (p48, $ISGF3\gamma$) form the ISGF3 complex that binds the ISRE in response to $IFN\alpha/\beta$ stimulation.

Numerous genes were identified that contain an ISRE. They represent components of the antiviral defense such as the poly-A-synthase (Zhou, et al. (1993) Cell 72:753-755; Hassel, et al. (1993) EMBO 12, no. 8:3927-3304) and the dsRNA activated protein kinase (PKR) (Katze, et al. (1991) Molecular Cellular Biology 11, no. 11:5497-5505), cell surface proteins such as ICAM (Dustin, et al. (1986) J Immunol. 137, no. 1:245-54; Marotta, et al. (1993) Blood. 81, no. 1:267-9) or the MHC class I and II molecules (Loh, et al. (1992) EMBO 11, no. 4:1351-1363), genes encoding chemokines such as RANTES, MCP, ISG15, IP10 (Reich, et al. (1987) Proc. Natl. Acad. Sci. USA 84:6394-6398; Luster, et al. (1987) Mol. Cell. Biol. 7:3723-3731), as well as many other genes with as of yet unknown functions such as ISG54, ISG56 (Lamer, et al. (1984) Proc. Natl. Acad. Sci. USA 81:6733-6737), GBP (Decker, et al. (1989) EMBO J 8:2009-2014) or 6-16 (Porter, et al. (1988) EMBO J. 7:85-92).

The inventor believes that the invention's compounds may operate is by inhibition of cytokine production via Interferon Regulatory Factor 3 activation. Vertebrates and invertebrates respond to bacterial or viral infection by activation of a defense mechanism that is part of the innate immune response. Viral infection is the major inducer of transcription of genes encoding various types of interferons. The ubiquitously expressed IRF3 has been found independently by several laboratories to be an important cellular response factor to viral infection. Infection of primary fibroblasts with human cytomegalovirus causes nuclear translocation of IRF3 and cooperative ISRE binding with the transcriptional co-activator CBP/p300. This is followed by subsequent induction of a distinct subset of ISRE containing genes (Navarro, et al. (1998) Mol. Cell. Biol. 18, no. 7:3796-3802). Other groups reported similar observations after infections of cells with Newcastle Disease Virus or Sendai Virus (Lin, et al. (1998) Mol Cell Biol. 18, no. 5:2986-96; Yoneyama, et al. (1998) EMBO J. 17, no. 4:1087-1095; Wathelet, et al. (1998) Molecular Cell 1:507-518). Activation of IRF-3 requires phosphorylation of several serine residues located in two clusters at the carboxy-terminus of the protein.

Innate immune recognition of bacterial infection is mediated by a system of germline-encoded receptors (Toll receptors) that recognize conserved molecular patterns associated with microbial pathogens such as bacterial cell wall lipopolysaccharides (LPS) (Kopp, et al. (1999) Curr Opin Immunol. 11, no. 1:13-8). These receptors, which are coupled to downstream signaling cascades that mediate the induction of immune-response genes, represent the most ancient host defense system found in mammals, insects and plants. In mammals, it is primarily monocytes and macrophages that respond to LPS, releasing cytokines and chemokines that provoke an inflammatory response. Excessive amounts of LPS can result in a fatal syndrome known as septic shock (Kopp, et al. (1999) Curr Opin Immunol. 11, no. 1:13-8).

The cytoplasmic tail of the Toll-like receptors is homologous to the intracellular region of the IL-1 receptor and is therefore referred to as the Toll/IL-1R homology (TIR) domain (Kopp, et al. (1999) Curr Opin Immunol. 11, no. 1:13-8). Significant progress has been made over the last few years in the identification of the signaling molecules involved in Toll/IL-1R induced gene expression, however, most of the work focused on the signaling pathway leading to the activation of the nuclear factor NFκB.

The inventor hypothesized that IRF3 activation represents a general cellular response to contact with pathogens, and investigated whether LPS would be able to initiate such a response; similar to viral activation, ISG induction by LPS involved the activation of IRF3, but not of an STAT proteins (Navarro, et al. (1999) J Biol Chem 274, no. 50:35535-8). In an effort to delineate the LPS mediated signaling cascade that leads to the phosphorylation of IRF3, the inventor found that the Tyk2 tyrosine kinase, a Jak family kinase involved in the type I interferon signaling pathway, is also rapidly activated in response to LPS. Interestingly, Tyk2-deficient macrophages fail to upregulate nitrogen oxide synthase (NOS) in response to LPS (Karaghiosoff, et al. (2000) Immunity 13, no. 4:549-60).

With respect to administration of the compounds of the invention to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors which those skilled in the art will recognize.

The dosage amount and frequency are selected to create an effective level of the compound without substantially harmful effects. When administered orally or intravenously, the dosage of a compound of any one of Formulae A-E will generally range from 0.001 to 1000 mg/Kg/day, more preferably from 0.01 to 100 mg/Kg/day, and most preferably from 0.1 to 10 mg/Kg/day. To achieve these concentrations in the subject, when intended for oral administration, the weight of any one of Formulae A-E may be from 0.01% to 90%, more preferably from 0.1% to 50%, and most preferably from 0.1% to 70% of the total weight of the composition. Preferred parenteral dosage units contain from 0.001% to 10%, more preferably from 0.01% to 10%, and most preferably from 0.01% to 1% by weight of any one of Formulae A-E. When administered intranasally or by inhalation, the dosage range may be from 0.001 to 100 mg/Kg/day, more preferably from 0.01 to 10 mg/Kg/day, and most preferably from 0.01 to 1 mg/Kg/day. Topical formulations may contain a concentration of the compound of any one of Formulae A-E of from 0.1% to 50% w/v (weight unit to volume unit), more preferably from 0.01% to 20% w/v, and most preferably from 0.1% to 10% w/v.

A pharmaceutically effective amount may be determined using in vitro and in vivo assays known in the art and disclosed herein. For example, with respect to reducing symptoms of inflammatory bowel disease, the efficacy of the invention's compounds of Formula A-E may be determined using adoptive transfer of $CD4^+CD45RB^{hi}$ cells and/or IL-10 knock-out mice in combination with physiological and histopathological analysis of the treated animals (Example 2). Referring to sepsis, septic shock, or endotoxic shock, murine animals (Example 1) and canine animals (Sevransky et al. (1997) J. Clin. Invest. 99:1966-1973) may be used as models. With respect to multiple sclerosis, $MBP-TCR^+/STAT^-$ mice may be used as described herein (Example 3). Animal models for asthma are also known in the art, such as the murine animal model disclosed herein (Example 4).

Methods of administering a pharmaceutically effective amount of the invention's compounds are well known in the art and include, without limitation, administration in parenteral, oral, intraperitoneal, intranasal, topical, sublingual, rectal, and vaginal forms. Parenteral routes of administration include, for example, subcutaneous, intravenous, intramuscular, intrasternal injection, and infusion routes.

The compounds of the invention may be administered before, concomitantly with, and/or after manifestation of one or more symptoms of a disease or condition. Also, the invention's compounds may be administered before, concomitantly with, and/or after administration of another type of drug or therapeutic procedure (e.g., surgery). For example, in the case of sepsis, the invention's compounds may be administered before, concomitantly with, and/or after administration of antibiotics.

Pharmaceutical compositions preferably comprise one or more compounds of the present invention associated with one or more pharmaceutically acceptable carrier, diluent or excipient. In preparing such compositions, the active ingredients are usually mixed with or diluted by an excipient or enclosed within such a carrier which can be in the form of a capsule or sachet in which the coating may be gelatin, sugar, shellac, and other enteric coating agents. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidone, cellulose, water, syrup, and methyl cellulose.

Pharmaceutically acceptable carriers are known in the art such as those described in, for example, Remingtons Pharmaceutical Sciences, Mack Publishing Co. (A. R. Gennaro edit. 1985). Exemplary pharmaceutically acceptable carriers are sterile saline, phosphate-buffered saline at physiological pH, polyethylene glycols, polypropylene copolymers, and water soluble gels.

Other compounds that may be included with the invention's compositions include, for example, diluents, fillers, salts, buffers, preservatives (e.g., sodium benzoate, sorbic acid and esters of p-hydroxybenzoic acid), stabilizers, dyes, antioxidants, flavoring agents, lubricating agents (such as talc, magnesium stearate and mineral oil), wetting agents, emulsifying and suspending agents, preserving agents such as methyl- and propylhydroxybenzoates, sweetening agents and/or flavoring agents.

The pharmaceutically acceptable carriers may be liquid, with the compositions being, for example, an oral syrup or injectable liquid. Compositions in solid or liquid form may include an agent which binds to the active component(s) and thereby assists in the delivery of the active components. Suitable agents which may act in this capacity include a monoclonal or polyclonal antibody, a protein or a liposome.

Alternatively, the pharmaceutical composition of the present invention may consist of gaseous dosage units, e.g., it may be in the form of an aerosol useful in, for example, inhalatory administration. The term "aerosol" is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The composition may be intended for rectal administration, for example in the form of a suppository which will melt in the rectum and release the drug. The composition for rectal administration may contain an oleaginous base as a suitable nonirritating excipient. Such bases include, without limitation, lanolin, cocoa butter and polyethylene glycol.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred compositions contain, in addition to the invention's compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

The pharmaceutical compositions may be prepared by methodology well known in the pharmaceutical art. A composition intended to be administered by injection can be prepared by combining the compound of any one of Formulae A-E with water so as to form a solution. A surfactant may be added to facilitate the formation of a homogeneous solution or suspension. Surfactants are compounds that non-covalently interact with the compound of any one of Formulae A-E so as to facilitate dissolution or homogeneous suspension of the active compound in the aqueous delivery system.

The "subject" to whom the compounds are administered includes any animal that is capable of developing symptoms of an autoimmune disease, inflammatory disease, and/or transplant rejection, and that one of ordinary skill in the art determine is in need (for any reason) of such administration. Preferably, the subject is a mammal. More preferably, the mammal includes, without limitation, human and non-human animals such simians, rodents, ovines, bovines, ruminants, lagomorphs, porcines, caprines, equines, canines, felines, ayes, etc. Preferred non-human animals are members of the Order Rodentia (e.g., mouse and rat). Thus, the compounds of the invention may be administered by human health professionals as well as veterinarians.

In one preferred embodiment, the subject is human, mouse, or canine. In a more preferred embodiment, the mouse is a C3H/HeJBir mouse having reduced levels of serum IL-10. The term "reduced levels of serum IL-10" refers to a quantity of IL-10 in serum that is less than the quantity in a corresponding control animal as determined by any statistical method of analysis. The "reduced levels of serum IL-10" refer to a quantity of IL-10 that is preferably at least 20% less, more preferably at least 50% less, yet more preferably at least 90% less, than the quantity in a corresponding control animal, and most preferably is at the background level of, or is undetectable by, a Western blot analysis of IL-10, by immunofluorescence of IL-10, by reverse transcription polymerase chain (RT-PCR) reaction for detection of IL-10 mRNA, or by in situ hybridization for detection of IL-10 mRNA. When a background level or undetectable level of IL-10 peptide or mRNA is measured, this may indicate that IL-10 is not expressed. A reduced level of IL-10 need not, although it may, mean an absolute absence of expression of IL-10. As disclosed herein, a C3H/HeJBir mouse having reduced levels of serum IL-10 is useful as a model for Crohn's disease.

In another preferred embodiment, the mouse has severe combined immunodeficiency (SCID). This mouse is useful as a model for colitis. In another embodiment the mouse is RAG1/2$^{-/-}$ mouse that is also useful as a model for colitis (Kawachi et al. (2000), supra). In yet another embodiment, the mouse is a MBP-TCR$^+$/STAT$^-$ mouse that is useful as a model for multiple sclerosis in humans. In a further embodiment, the subject is canine. Canine models are accepted in the art as models for sepsis, septic shock, or endotoxic shock (Sevransky et al. (1997) J. Clin. Invest. 99:1966-1973).

EXPERIMENTAL

The following examples serve to illustrate certain preferred embodiments and aspects of the present invention and are not to be construed as limiting the scope thereof.

Example 1

Piceatannol Inhibits Toxic Shock in a Mouse Animal Model for Septic Shock

The inventor established that micromolar concentrations of piceatannol are capable of blocking lipopolysaccharide (LPS) induced gene expression (such as RANTES, MCP-1, and ISG54). Based on these results, the effect of piceatannol on endotoxic shock was investigated. Endotoxic shock was induced by intraperitoneal injection of 1 µg LPS into laboratory mice in the presence of 20 mg D-galactosamine (D-Gal). This regimen leads to a 90-100% lethality rate by 9-12 hours post injection. The following data in Tables 1-3 reports the mortality rate over 28 days of observation. In one experiment, animals were treated intra peritoneally with piceatannol. The results are shown in Table 1.

TABLE 1

Table 1
Piceatannol Administered intraperitoneally prevents
septic shock in high and low dose animal model

| LPS (intraperitoneal) | Piceatannol (µg) | Lethality rate |
|---|---|---|
| 1 µg (+D-Gal) | — | 14/16 |
| — | 1000 | 0/8 |

TABLE 1-continued

Table 1
Piceatannol Administered intraperitoneally prevents
septic shock in high and low dose animal model

| LPS (intraperitoneal) | Piceatannol (µg) | Lethality rate |
|---|---|---|
| 1 µg (+D-Gal) | 250 | 5/12 |
| 1 µg (+D-Gal) | 500 | 0/8 |
| 1000 µg | — | 9/9 |
| 1000 µg | 500 → 1000 | 3/8 |

In another experiment, piceatannol was administered intraperitoneally and/or intravenously as shown in Table 2.

TABLE 2

Table 2
Piceatannol Administered intraperitoneally and/or intravenously prevents septic shock in high and low dose animal model

| LPS + D-Gal (ip) | Piceatannol (µg) | Lethality rate | |
|---|---|---|---|
| 1 µg | — | 10/12 | ** |
| — | 1000 (ip) | 0/6 | |
| — | 1000 (iv) | 0/2 | |
| 1 µg | 250 (ip) | 3/8 | |
| 1 µg | 400 (ip) | 0/2 | |
| 1 µg | 250 (iv) + 250 (ip) | 0/6 | ** |

The data in Tables 1 and 2 demonstrate that piceatannol displays very low toxicity in vivo. Mice that had received piceatannol alone showed no signs of acute (i.e., within 2 hours post-injection) toxicity, even at the highest doses (1 mg piceatannol, intraperitoneal or intravenously). All animals that received piceatannol (with or without subsequent LPS injection) have been monitored for several weeks, and thus far show no signs of delayed toxicity either. The data also shows that a single administration of piceatannol by either the intravenous or intraperitoneal routes significantly reduced death associated with endotoxic shock, and that combined intravenous and intraperitoneal administration of piceatannol provided up to 100% protection against endotoxic shock.

In another experiment, 1 mg of LPS was administered intraperitoneally. Piceatannol or tetramethoxy-piceatannol (TMP) were administered intraperitoneally prior to LPS treatment, with some mice receiving subcutaneous doses of either piceatannol or TMP following LPS administration. The results are shown in Table 3.

TABLE 3

Table 3
Piceatannol and tetramethoxy-piceatannol (TMP) administered
intraperitoneally and/or subcutaneously prevent septic shock in high
dose (1000 µg LPS) and low dose (1 µg LPS + D-Gal) animal model

| | Low Dose Model | High Dose Model |
|---|---|---|
| LPS alone | 63 dead/72 total 88% | 41 dead/48 total 85% |
| LPS + Piceatannol | | |
| 400 µM | 10 dead/21 total 48% | |
| 1000 µM | 7 dead/20 total 35% | |
| LPS + TMP | | |
| 1000-1250 µM | 9 dead/24 total 38% | |

TABLE 3-continued

Table 3
Piceatannol and tetramethoxy-piceatannol (TMP) administered intraperitoneally and/or subcutaneously prevent septic shock in high dose (1000 μg LPS) and low dose (1 μg LPS + D-Gal) animal model

|  | Low Dose Model | High Dose Model |
|---|---|---|
| LPS + Piceatannol | | |
| 1000 μM pre, 500 μM SC post every 12 | | 8 dead/16 total 50% |
| LPS + 1 TMP | | |
| 1000 μM pre, 500 μM SC post every 12 | | 7 dead/16 total 44% |

The results in Table 3 show that intraperitoneal administration of piceatannol or tetramethoxy-piceatannol prior to LPS challenge had a prophylactic effect by significantly reducing mortality that is caused by septic shock. The results in Table 3 also demonstrate that intraperitoneal administration of piceatannol or tetramethoxy-piceatannol prior to LPS challenge coupled with subcutaneous administration of piceatannol or tetramethoxy-piceatannol following LPS challenge significantly reduced mortality that is caused by septic shock.

Example 2

Treatment and Evaluation of Animal Models of Inflammatory Bowel Disease (IBD)

The following animal models of IBD, approaches to exemplary treatment and scoring of animal treated models are used to test the potential efficacy of compounds of the invention.

A. Animal Models

1. IL-10 Knock-Out Mice:

IL-10 plays a crucial role in the pathogenesis of Crohn's disease (Schreiber, et al. (1995) Gastroenterology 108, no. 5:1434-44). Patients suffering from Crohn's disease display reduced serum levels of IL-10 (Kucharzik, et al. (1995) Clin Exp Immunol 100, no. 3:452-6). Importantly, IL-10 deficient mice spontaneously develop colitis by the age of 3 month (Davidson, et al. (1996) J Exp Med 184, no. 1:241-51; Madsen, et al. (2001) Clin Invest Med 24, no. 5:250-7). While IL-10 deficiency is clearly triggering the onset of IBD, other genetic factors contribute to the disease progression. This is evidenced by the fact that IL-10-deficient C3H/HeJBir mice (Jackson Laboratories, Maine, USA) developed early onset colitis in contrast to IL-10-deficient C57BL/6J mice. Commercially available IL-10-deficient C3H/HeJBir mice will be utilized since these animals develop colitis spontaneously, this model requires minimal experimental handling, and is thus efficient for the initial evaluation of the test compounds. This animal model allows evaluation of whether the test compounds suppress disease progression while the animals are receiving treatment.

2. Adoptive Transfer of $CD4^+CD45RB^{hi}$ Cells

Colitis development in this model is based on the transfer of $CD4^+CD45RB^{hi}$ cells isolated from wildtype mice into SCID or $RAG1/2^{-/-}$ [Jong et al. (2001) Nature Immunology 2(11):1061-1066] recipients as described by Kawachi et al. (Kawachi, et al. (2000) BBRC 268, no. 2:547-52). Briefly, spleens will be isolated from wildtype CB-17 mice (Taconic), and $CD4^+$ cells enriched by negative depletion with B220, $CD8^+$ and Mac-1 antibodies on the MACS system, and $CD4^+$ $CD45RB^{hi}$ cells will be isolated from the enriched $CD4^+$ cell population by FACS sorting (UCSD Flow cytometry core).

Six to eight weeks after the transfer of $CD4^+CD45RB^{hi}$ cells into SCID CB-17 mice (Taconic), the animals develop severe colitis. In contrast to the above-discussed IL-10 deficient model mice, this model provides an autoimmune disease model that is not based on a genetic defect, thus it allows determination of not only whether treatment with the test compound results in the suppression of disease progression, but also whether it leads to a cure of the colitis in these animals. Thus, this model is useful to confirm and extend the findings obtained with the IL-10 deficient mouse model.

B. Treatment of Animals

IL10-deficient mice will be observed for the onset of IBD (~3 month). Animals that display a weight loss of >10% and suffer from loose stools/bleeding will be used in the study. The treatment group (60 animals; 20 animal per compound) will receive 1 mg of piceatannol, resveratrol or TMP subcutaneously (s.c.) in PBS daily (This is the dosage that was found to be effective in the sepsis and EAE models. Once an effect of the drugs has been established, we will identify the lowest efficient dosage for each of the three compounds). Controls (20 animals) will receive equal volume of PBS. All animals will be monitored and weighed daily. At the time the control animals progress to the moribund stage and have to be sacrificed, half of the animals (randomly selected) in each treated group will also be sacrificed for histological analysis. The remaining treated mice will be kept for continuous monitoring until they progress to the moribund stage, but not longer than 60 days.

Once a test compound has been determined to offer potential in inhibiting IBD progression in the IL10-deficient model, we will further confirm the results in the $CD4^+CD45RB^{hi}$ cell transfer model. Twenty $CD4^+CD45RB^{hi}$ cell-recipient animals that meet the above listed inclusion criteria for IBD will receive daily s.c. injections with the test compound that is found active in the IL10-deficient model. Ten control animals will receive equal volume of PBS. At the time the control animals progress to the moribund stage and have to be sacrificed, half of the animals (randomly selected) in the treated group will also be sacrificed for histological analysis. The remaining treated mice will be kept for continuous monitoring until they progress to the moribund stage. If no such disease progression occurs, the treatment will be discontinued after 60 days, and the animals continued to be observed to determine whether the inflammatory processes resume.

While evaluating the test compounds found most effective in the IL10-deficient model after parenteral administration in the $CD4^+CD45RB^{hi}$ cell transfer model, we will at the same time test the efficacy of the test compounds after oral administration in IL10-deficient mice. These experiments will be conducted identically to those outlined above for s.c. application, except that the test compounds will be administered orally. We will adhere to the exemplary dosage of 1 mg daily with other compounds. While the inventor expects a reduced systemic availability of the drugs after oral administration (e.g. the reported intestinal absorption rate for resveratrol in ~20%), nonetheless, the higher local concentration of the test compound in the intestine as the site of inflammation may compensate for that, and indeed may be even be advantageous.

C. Disease Scoring and Analysis

All animals in the study will be observed and weighed daily. In addition, the mice will be monitored for signs of loose stools or diarrhea, as will as for rectal bleeding.

The histopathological analysis of the proximal, middle and distal colon sections will be performed by the UCSD Pathology Core Facility. This approach will not only facilitate the cost-effective evaluation of the tissue sections by a trained pathologist, but will also ensure assigning of the grades in a blinded manner. The disease activity may be scored using the following exemplary criteria.

TABLE 4

Scoring Animals Treated With The Invention's Compounds

| | LIVE ANIMALS | | | HISTOLOGY | | |
|---|---|---|---|---|---|---|
| | | | | Colon | | Inflammation |
| Score | Weight Loss | Stool | Bleeding | weight (mg/cm) | Crypt damage | (% area affected) |
| 1 | 0-5% | Normal | Normal | <45 | Intact | 0-15% |
| 2 | 5-15% | Loose | Occult | 45-55 | Loss of basal ⅔ of crypts | 15-50% |
| 3 | >15% | Diarrhea | Gross bleeding | >55 | Severe erosion | >50% |

Example 3

Piceatannol Inhibits Autoimmune Encephalomyelitis (EAE) in a Mouse Model for Human Multiple Sclerosis (MS)

Experimental autoimmune encephalomyelitis (EAE) represents a murine model for multiple sclerosis, a TH1 cells mediated demyelinating autoimmune disorder. In this modes, STAT1-deficient mice (Jackson Laboratories, Maine, USA) were crossed with mice carrying a tansgenic T cell receptor against Myelin Basis Protein (MBP) [Lafaille et al. (1994) Cell 78(3):399-408]. The resulting MBP-TCR$^+$/STAT1$^-$ mice, when on an H2b/u or H2u/u background develop spontaneous paralysis. Typically, in this transgenic system, the disease progresses from early signs of hind leg paralysis (level 2) to the moribund stage of lethal paralysis (level 5) within 4-5 days.

Figure 10:
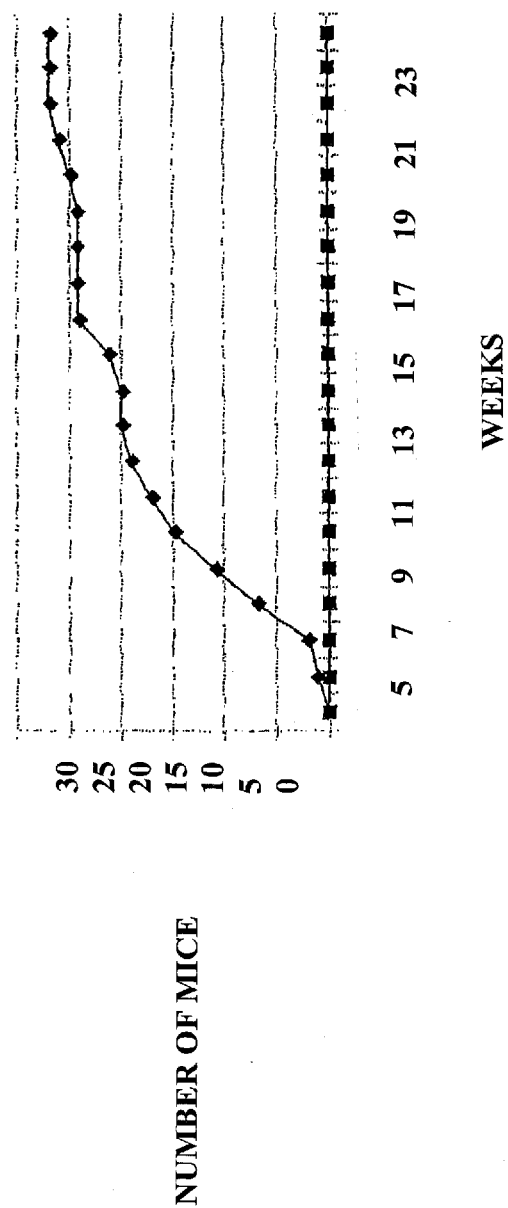
FIG. 10 shows the number of ST1−/− mice (filled diamonds) and ST1+/− mice (filled squares) over time.

Three mice showing clear signs of hind leg paralysis were injected s.c. with 1 mg piceatannol every 48 hours (FIG. 10). Under this regimen these animals survived for 30 days, at which time piceatannol administration was stopped. Ten days later animals had succumbed to complete paralysis and died (while transgenic animals cannot be cured because of their genetic defect, the disease was completely halted for the duration of administration of piceatannol). These findings demonstrate that piceatannol is highly effective in the treatment of the exemplary autoimmune disease of multiple sclerosis.

Example 4

Figure 11:
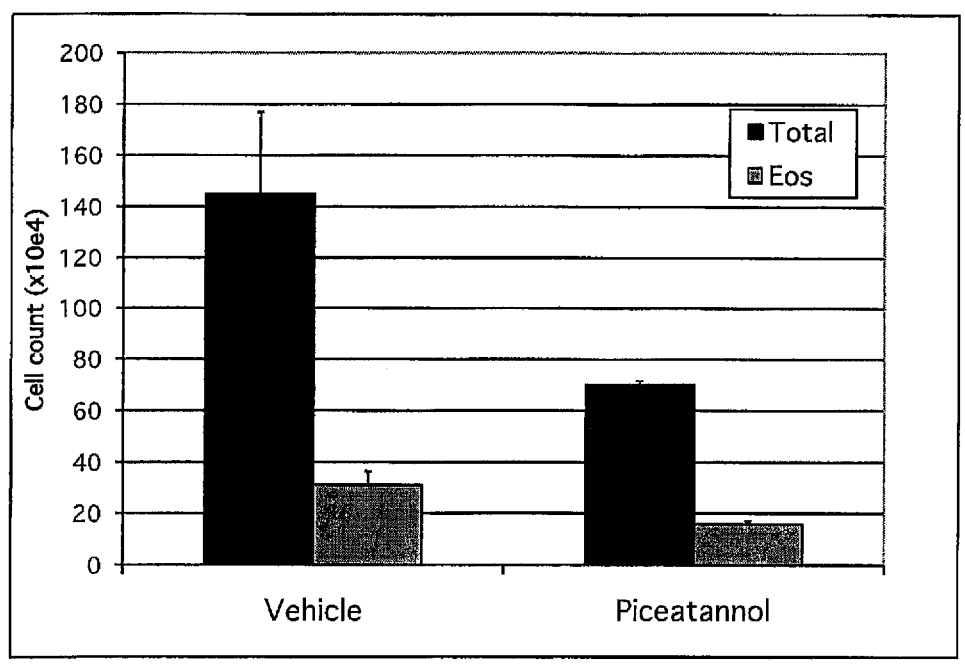
FIG. 11 shows the number of total lymphocytes and eosinophils infiltrating bronchioalveolar lavage fluid in animals treated with or without piceatannol.

Piceatannol Reduces Lymphocyte and Eosinophil Infiltration in a Mouse Animal Model for Asthma Mice (8 animals) were immunized by intraperitoneal (i.p.) injection of Ovalbumin after 2 weeks, The OA solution was administered into the nasal passage by inhalation without (4) or with (4) concurrent piceatannol regimen (1 mg i.p. daily). FIG. 11 shows that piceatannol administration resulted in a significant reduction in both lymphocytes and eosinophils infiltration into the lungs. This demonstrates that the exemplary piceatannol is useful in the treatment of asthma.

From the above, it is clear that the invention provides compositions and methods for the prevention, amelioration, and treatment of autoimmune disease, inflammatory disease, and/or transplant rejection by the administration to a subject in need thereof a pharmaceutically effective amount of a purified compound of any one of Formulae A-E.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiment, it should be understood that the invention as claimed should not be unduly limited to such specific embodiment. Indeed, various modifications of the described modes for carrying out the invention which are obvious to those skilled in the art and in fields related thereto are intended to be within the scope of the following claims.

The invention claimed is:

1. A method for reducing one or more symptoms of multiple sclerosis in a subject, wherein said method comprises administering to said subject a pharmaceutically effective amount of purified piceatannol (3,3',4,5'-tetrahydroxy trans stilbene), wherein said subject is selected from the group consisting of human, mouse and canine.

2. The method of claim 1, wherein said administering is selected from the group consisting of parenteral, oral, and intraperitoneal.

3. The method of claim 1, wherein said administering is before manifestation of one or more symptoms of multiple sclerosis.

4. The method of claim 1, wherein said administering is concomitant with manifestation of one or more symptoms of multiple sclerosis.

5. The method of claim 1, wherein said administering is after manifestation of one or more symptoms of multiple sclerosis.

6. The method of claim 1, wherein said one or more symptoms comprise paralysis.

* * * * *